(12) United States Patent
Adams et al.

(10) Patent No.: US 11,712,246 B2
(45) Date of Patent: Aug. 1, 2023

(54) METHOD FOR CONTROLLING CUTTING MEMBER ACTUATION FOR POWERED SURGICAL STAPLER

(71) Applicant: Cilag GmbH International, Zug (CH)

(72) Inventors: Shane R. Adams, Lebanon, OH (US); Thomas E. Adams, Loveland, OH (US); Nicholas J. Ross, Franklin, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 87 days.

(21) Appl. No.: 17/410,604

(22) Filed: Aug. 24, 2021

(65) Prior Publication Data
US 2022/0079598 A1 Mar. 17, 2022

Related U.S. Application Data

(63) Continuation of application No. 16/574,797, filed on Sep. 18, 2019, now Pat. No. 11,123,074.

(51) Int. Cl.
| | |
|---|---|
| *A61B 17/115* | (2006.01) |
| *A61B 17/072* | (2006.01) |
| *A61B 17/11* | (2006.01) |
| *A61B 17/00* | (2006.01) |

(52) U.S. Cl.
CPC .... *A61B 17/1155* (2013.01); *A61B 17/07207* (2013.01); *A61B 17/1114* (2013.01); *A61B 2017/00398* (2013.01); *A61B 2017/00477* (2013.01); *A61B 2017/00734* (2013.01); *A61B 2017/07257* (2013.01); *A61B 2017/1132* (2013.01); *A61B 2017/1135* (2013.01); *A61B 2017/1139* (2013.01)

(58) Field of Classification Search
CPC .......... A61B 17/1155; A61B 17/07207; A61B 17/1114
See application file for complete search history.

(56) References Cited

U.S. PATENT DOCUMENTS

| | | |
|---|---|---|
| 5,205,459 A | 4/1993 | Brinkerhoff et al. |
| 5,271,544 A | 12/1993 | Fox et al. |
| 5,275,322 A | 1/1994 | Brinkerhoff et al. |

(Continued)

OTHER PUBLICATIONS

U.S. Appl. No. 62/868,457, entitled "Surgical Systems with Multiple RFID Tags," filed Jun. 28, 2019.

*Primary Examiner* — Nathaniel C Chukwurah
(74) *Attorney, Agent, or Firm* — Frost Brown Todd LLP

(57) ABSTRACT

A method is provided for operating a powered surgical stapler having a motor unit, a controller. and a stapling assembly having a closure member, a staple driver member, and a knife member. The controller receives a user input that indicates a tissue gap to be defined by the stapling assembly in a closed state. Based on the user input, the controller controls the motor unit to actuate the closure member to transition the stapling assembly to the closed state to define the tissue gap and clamp tissue therein. The controller then controls the motor unit to actuate the staple driver member to drive staples into the clamped tissue. In response to determining that the staple driver member has reached a predetermined longitudinal position, the controller controls the motor unit to initiate actuation of the knife member to cut the clamped tissue.

20 Claims, 22 Drawing Sheets

(56) References Cited

U.S. PATENT DOCUMENTS

| | | | |
|---|---|---|---|
| 5,285,945 | A | 2/1994 | Brinkerhoff et al. |
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 8,910,847 | B2 | 12/2014 | Nalagatla et al. |
| 9,445,816 | B2 | 9/2016 | Swayze et al. |
| 9,463,022 | B2 | 10/2016 | Swayze et al. |
| 9,532,783 | B2 | 1/2017 | Swayze et al. |
| 9,597,081 | B2 * | 3/2017 | Swayze ............... A61B 17/1155 |
| 10,045,780 | B2 | 8/2018 | Adams et al. |
| 10,307,157 | B2 | 6/2019 | Miller et al. |
| 11,123,074 | B2 | 9/2021 | Adams et al. |
| 11,185,324 | B2 | 11/2021 | Adams et al. |
| 11,185,331 | B2 | 11/2021 | Adams et al. |
| 2008/0185419 | A1 | 8/2008 | Smith et al. |
| 2010/0258611 | A1 * | 10/2010 | Smith ................... A61B 17/068 227/175.1 |
| 2013/0214025 | A1 | 8/2013 | Zemlok et al. |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2017/0258471 | A1 * | 9/2017 | DiNardo ............ A61B 17/1155 |
| 2018/0368836 | A1 | 12/2018 | Auld et al. |
| 2021/0077111 | A1 | 3/2021 | Adams et al. |

* cited by examiner

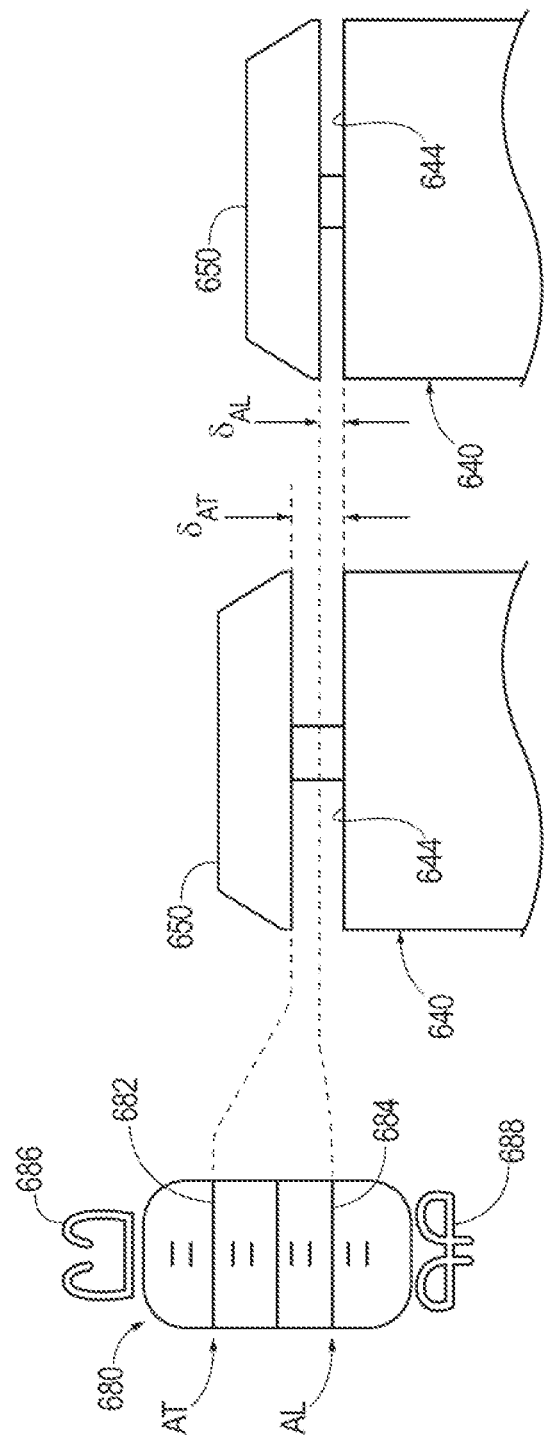

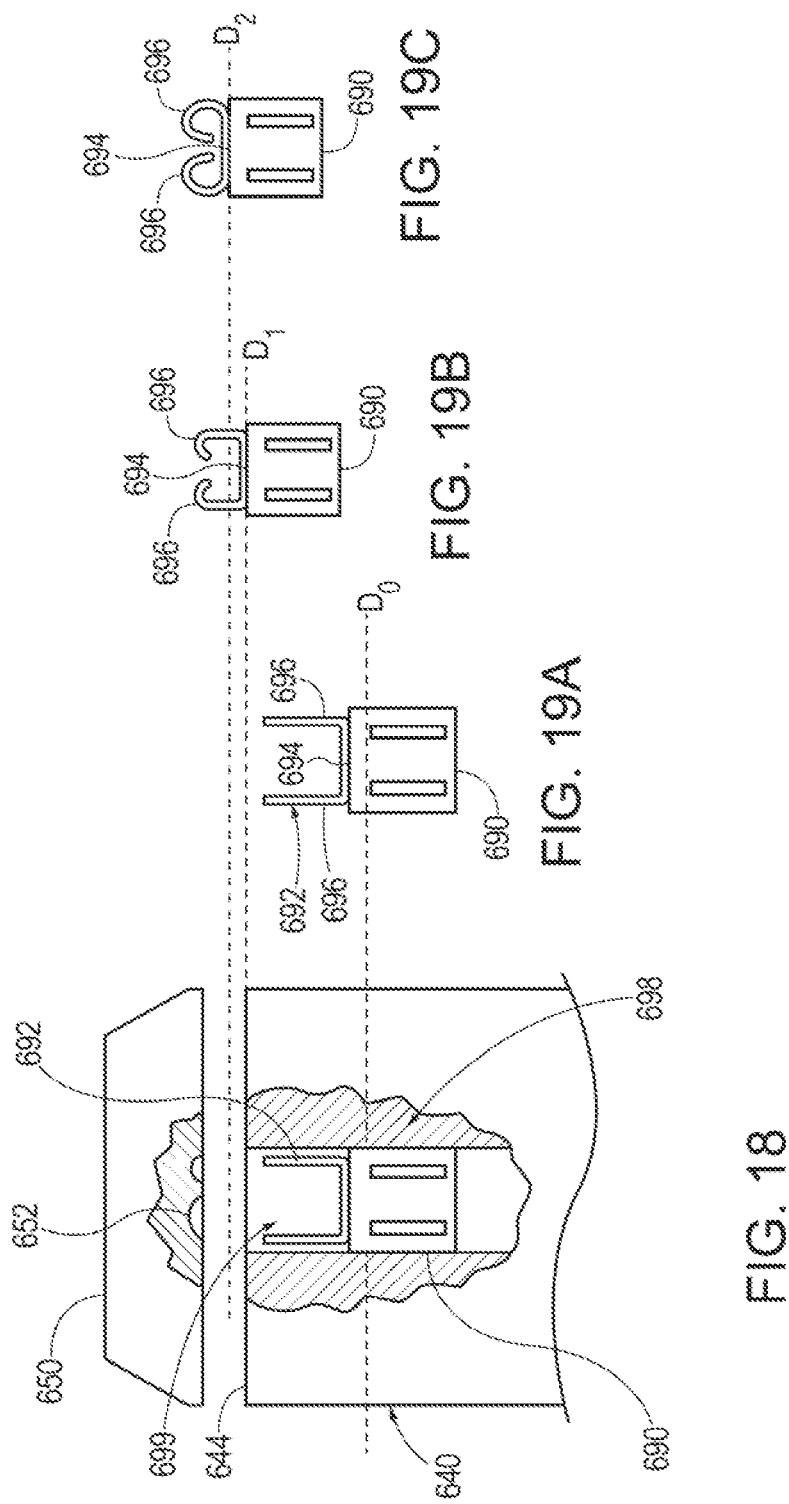

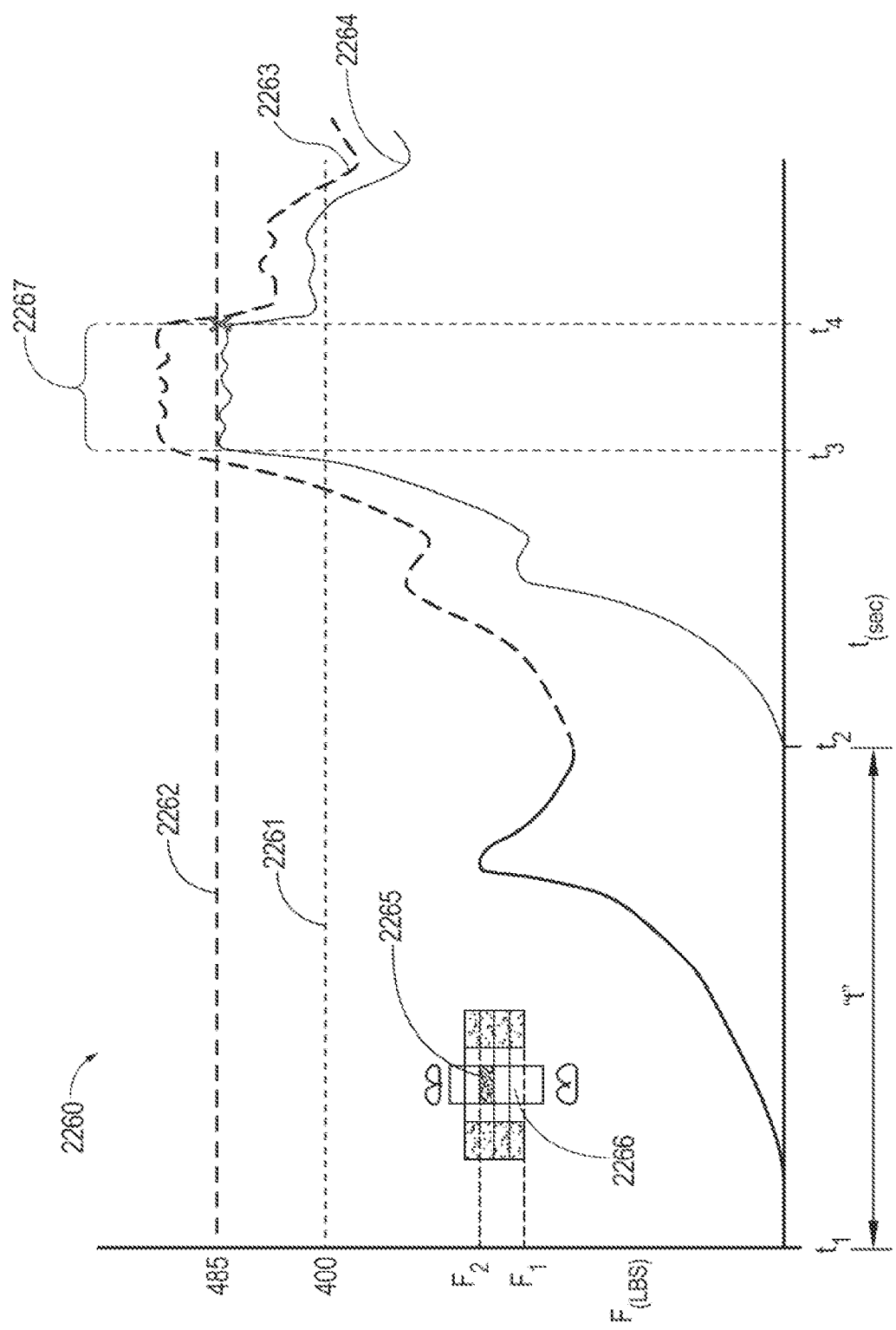

METHOD FOR CONTROLLING CUTTING MEMBER ACTUATION FOR POWERED SURGICAL STAPLER

This application is a continuation of U.S. patent application Ser. No. 16/574,797, entitled "Method for Controlling Cutting Member Actuation for Powered Surgical Stapler," filed Sep. 18, 2019 and issued as U.S. Pat. No. 11,123,074 on Sep. 21, 2021.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 depicts a schematic view of a graphical indicator of a user interface feature of the circular surgical stapler of FIG. 9, showing exemplary first and second tissue gap settings for the anvil;

FIG. 17A depicts a schematic side view of the stapling head assembly and anvil of the circular surgical stapler of FIG. 9, showing the anvil positioned to define a first, larger tissue gap corresponding to the first tissue gap setting of FIG. 16;

FIG. 17B depicts a schematic side view of the stapling head assembly and anvil of the circular surgical stapler of FIG. 9, showing the anvil positioned to define a second, smaller tissue gap corresponding to the second tissue gap setting of FIG. 16;

FIG. 18 depicts a schematic side elevational view of the stapling head assembly and anvil of the circular surgical stapler of FIG. 9, showing side portions cutaway to reveal a staple driver and a corresponding staple housed within a respective staple opening of the stapling head assembly, showing the staple driver and staple in a fully recessed position;

FIG. 19A depicts a side elevational view of the staple driver and staple of FIG. 18, showing the staple driver and staple in the fully recessed proximal position;

FIG. 19B depicts a side elevational view of the staple driver and staple of FIG. 18, showing the staple driver and staple in a partially extended intermediate position in which an upper end of the staple driver and a crown of the staple are positioned at a deck surface of the stapling head assembly and staple;

FIG. 19C depicts a side elevational view of the staple driver and staple of FIG. 18, showing the staple driver and staple in a fully extended distal position in which legs of the staple are fully formed by the anvil;

FIG. 21 depicts a line graph showing firing loads over time for the circular surgical stapler of FIG. 9 in accordance with two different firing algorithms.

Figure 1:
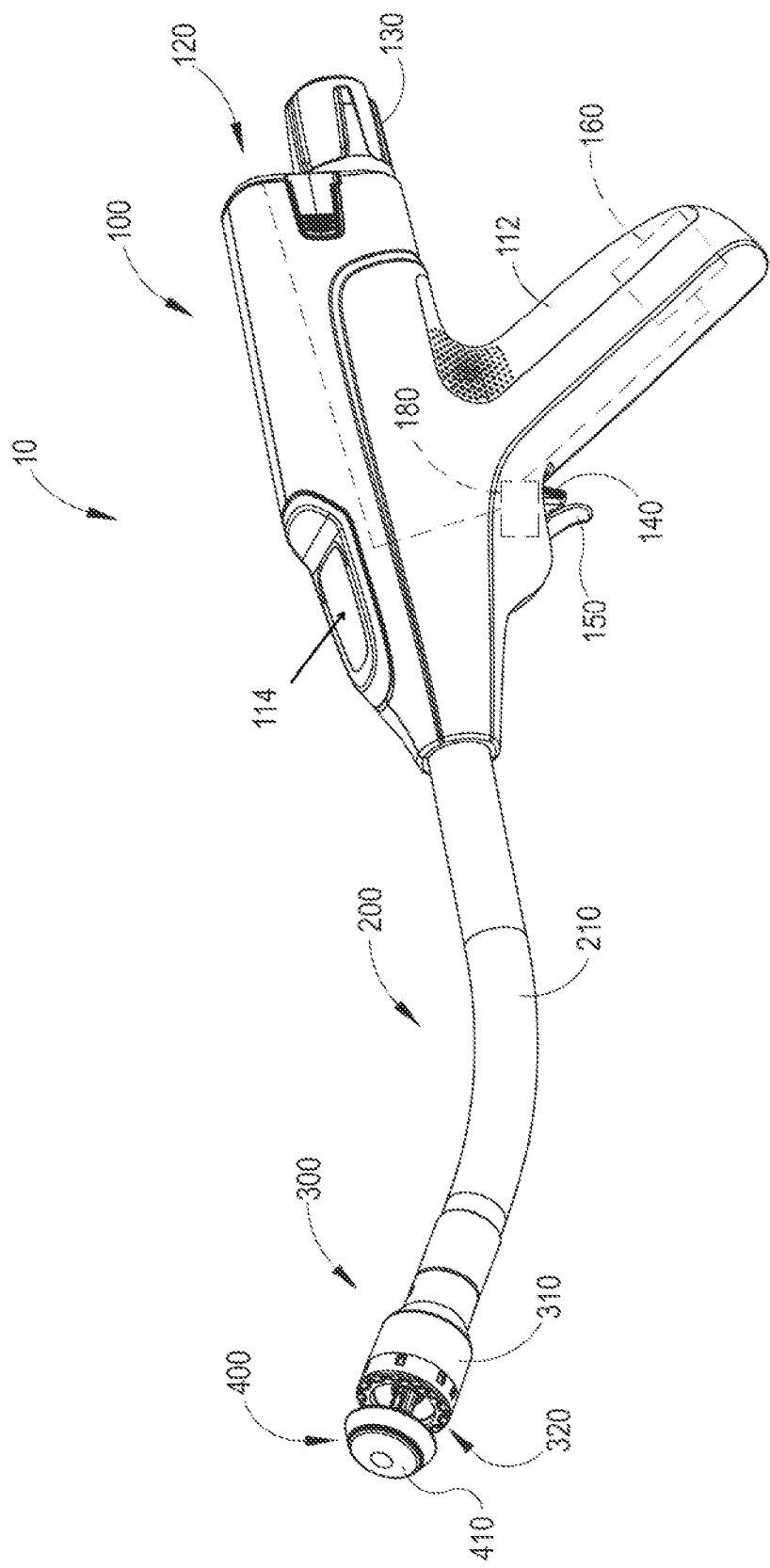
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Overview of Exemplary Circular Surgical Stapling Instrument

Figure 2:
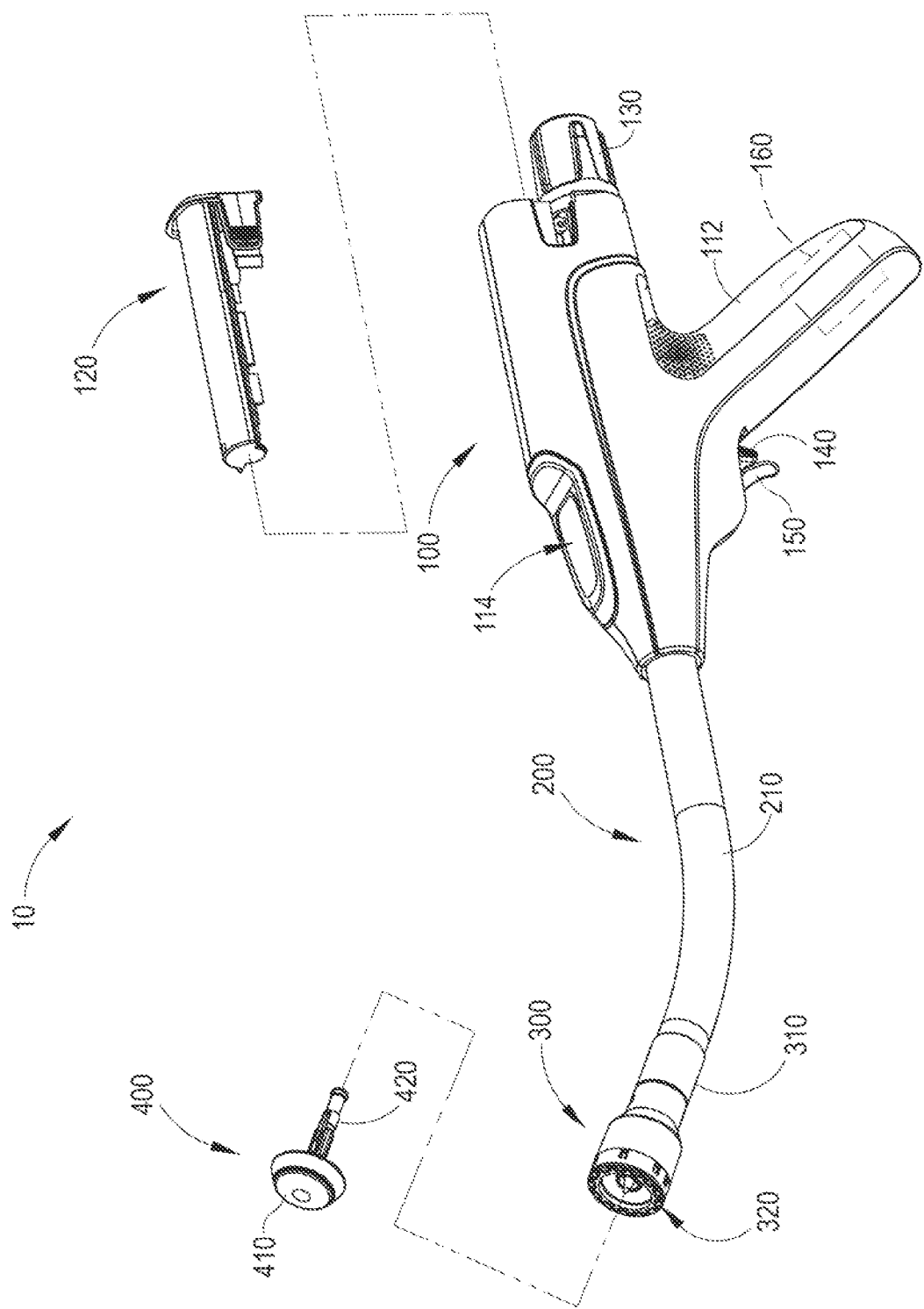
FIG. 2 depicts a perspective view of the circular stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
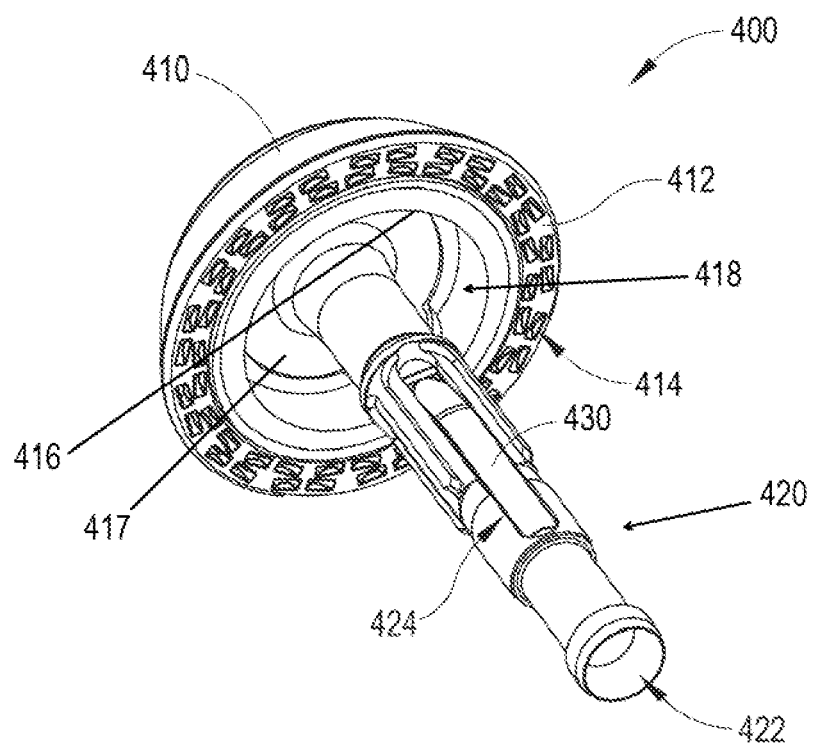
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to pivot radially inwardly toward the longitudinal axis defined by shank (420). Latch members (430) thus act as retaining clips. This allows anvil (400) to be removably secured to an actuatable closure member in the form of a trocar (330) of stapling head assembly (300), as will be described in greater detail below. It should be understood, however, that latch members (436) are merely optional. Anvil (400) may be removably secured to trocar (330) using any other suitable components, features, or techniques.

B. Exemplary Stapling Head Assembly

Figure 4:
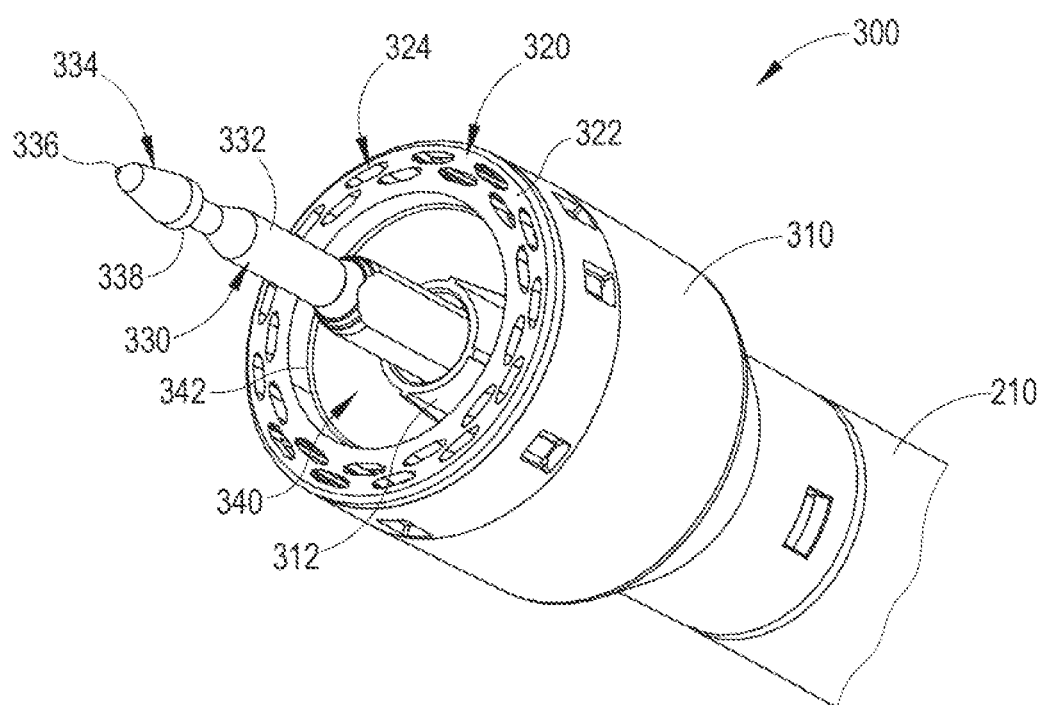
FIG. 4 depicts a perspective view of the stapling head assembly of the circular stapler of FIG. 1.
Figure 5:
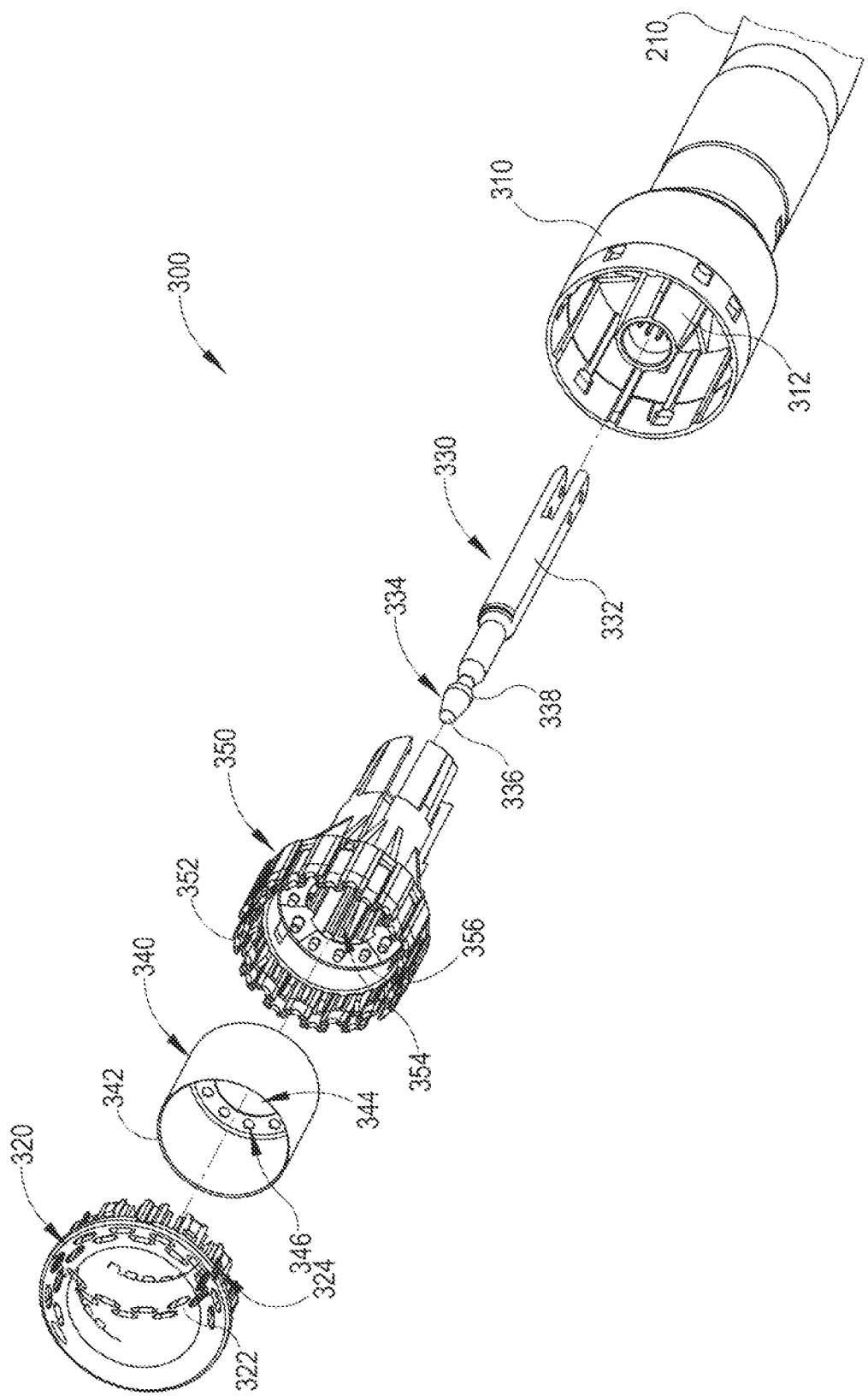
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those of ordinary skill in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

Figure 9:
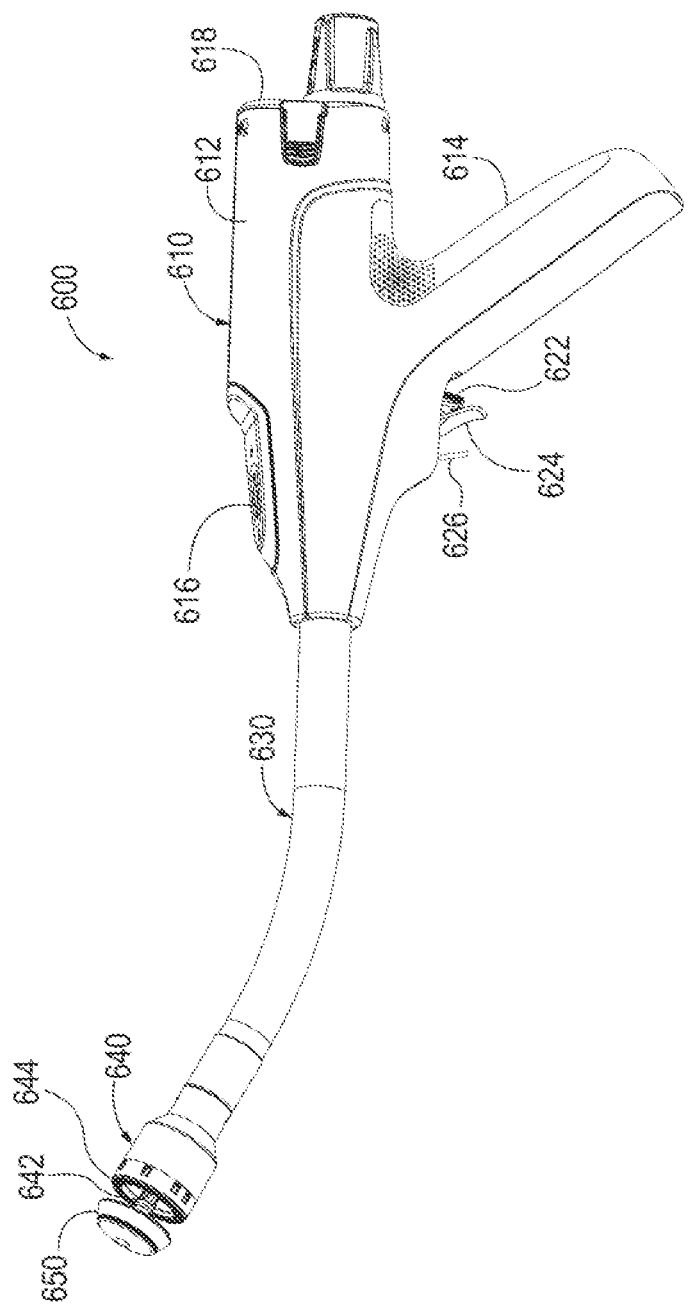
FIG. 9 depicts a perspective view of another exemplary circular surgical stapler.

As best seen in FIG. 9, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition, or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, issued as U.S. Pat. No. 10,709,452 on Jul. 14, 2020 the disclosures of which are incorporated by reference herein.

C. Exemplary Shaft Assembly

Figure 6:
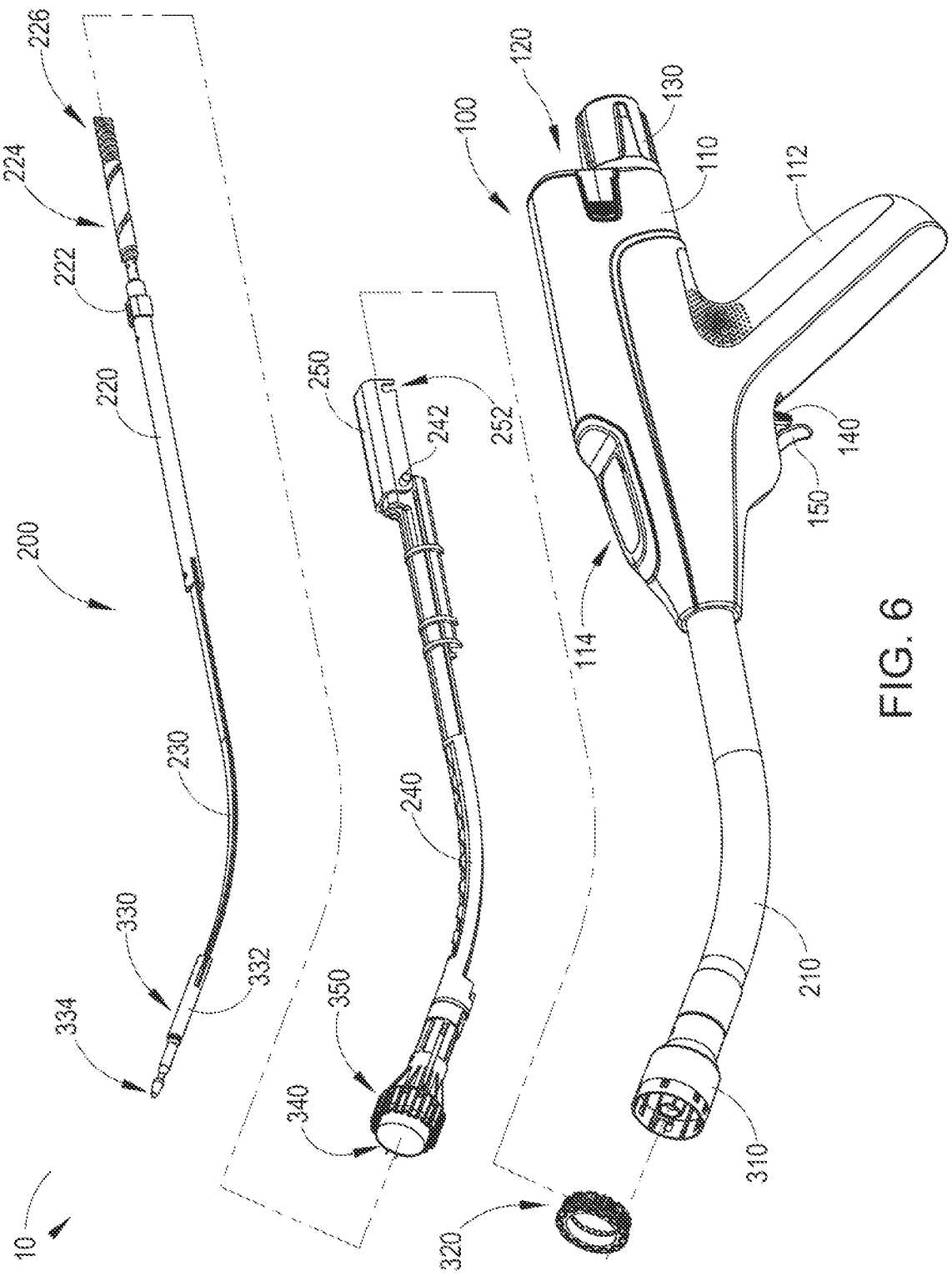
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, issued as U.S. Pat. No. 10,709,452 on Jul. 14, 2020, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, issued as U.S. Pat. No. 10,709,452 on Jul. 14, 2020, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
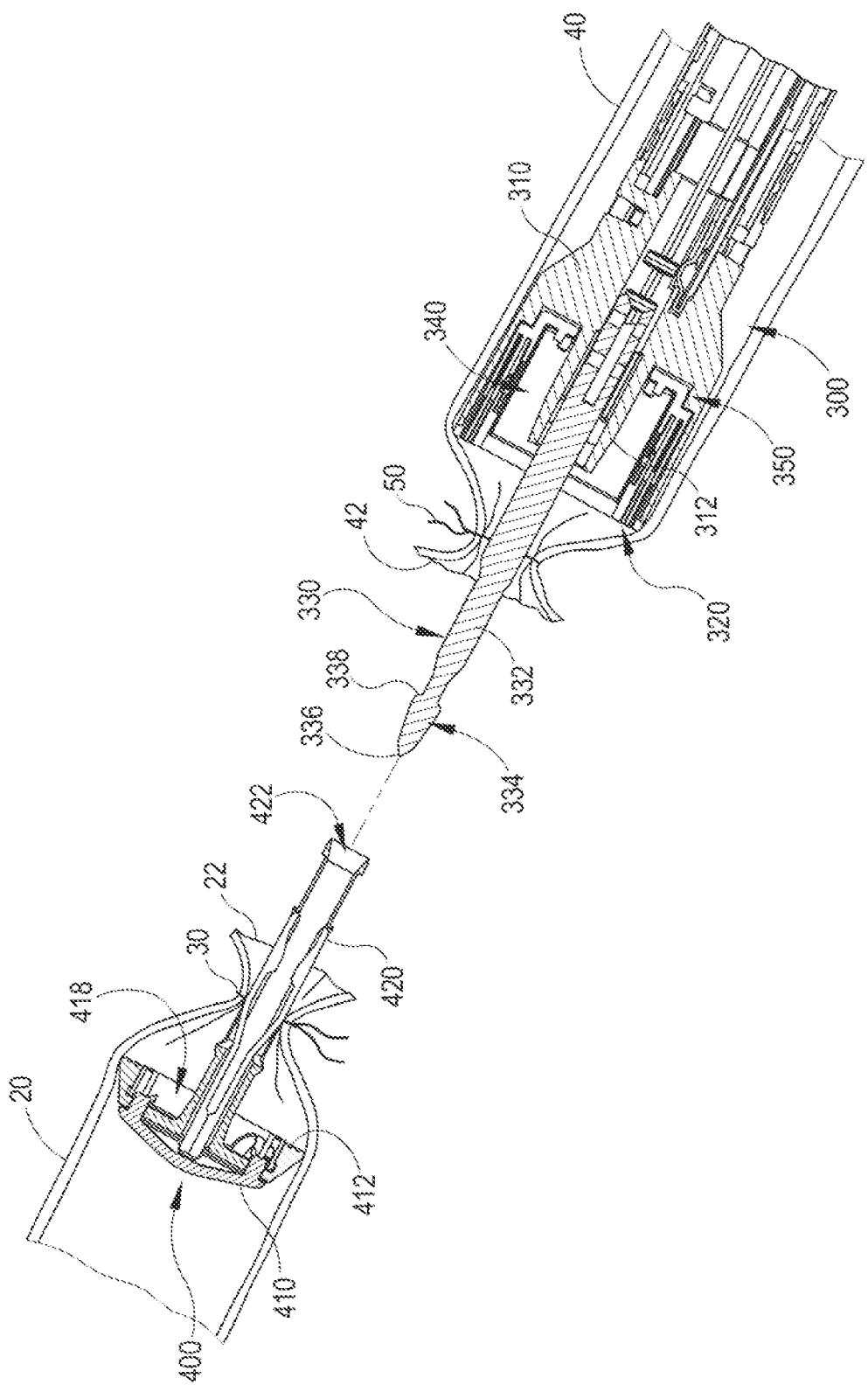
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
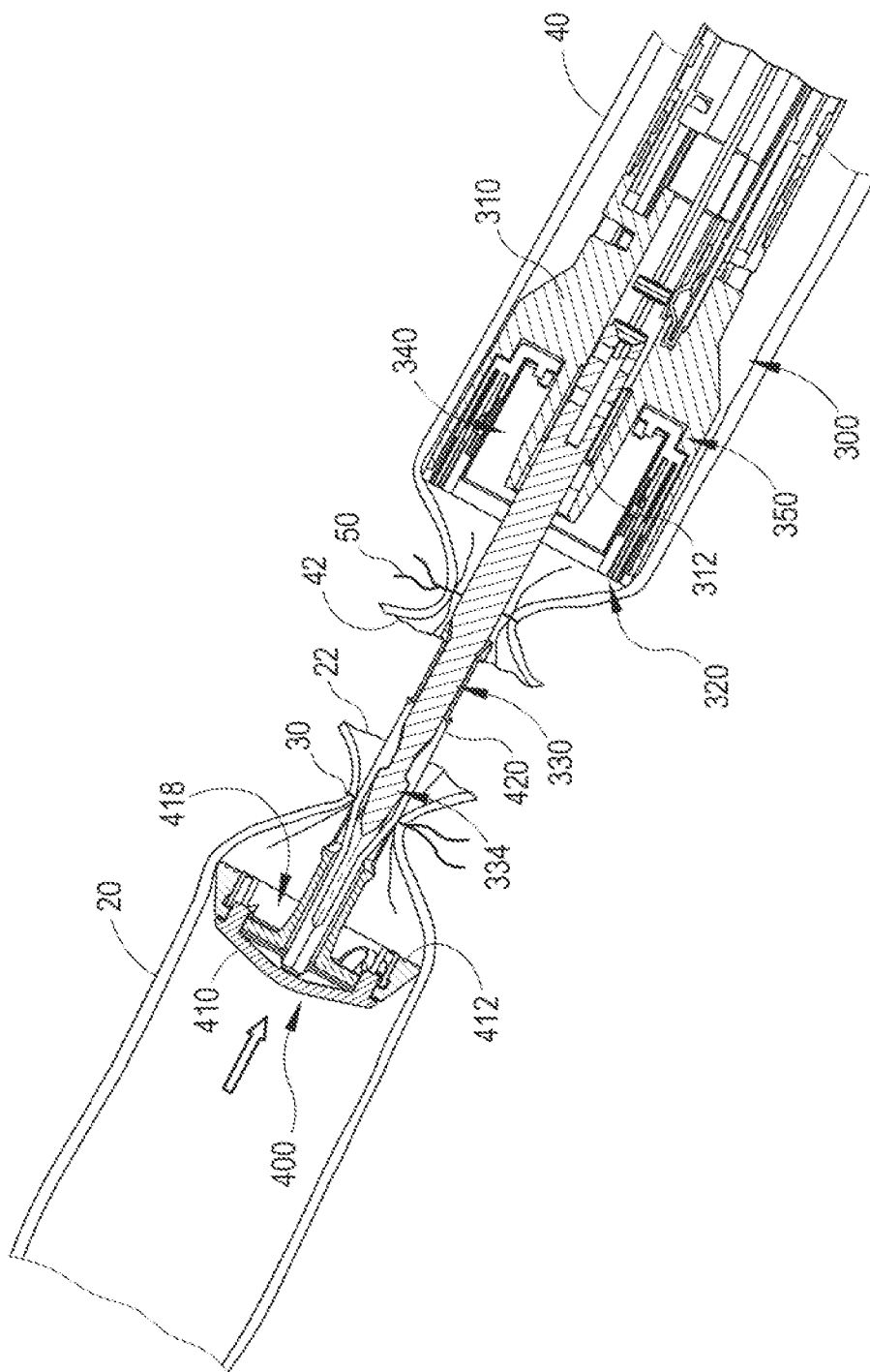
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
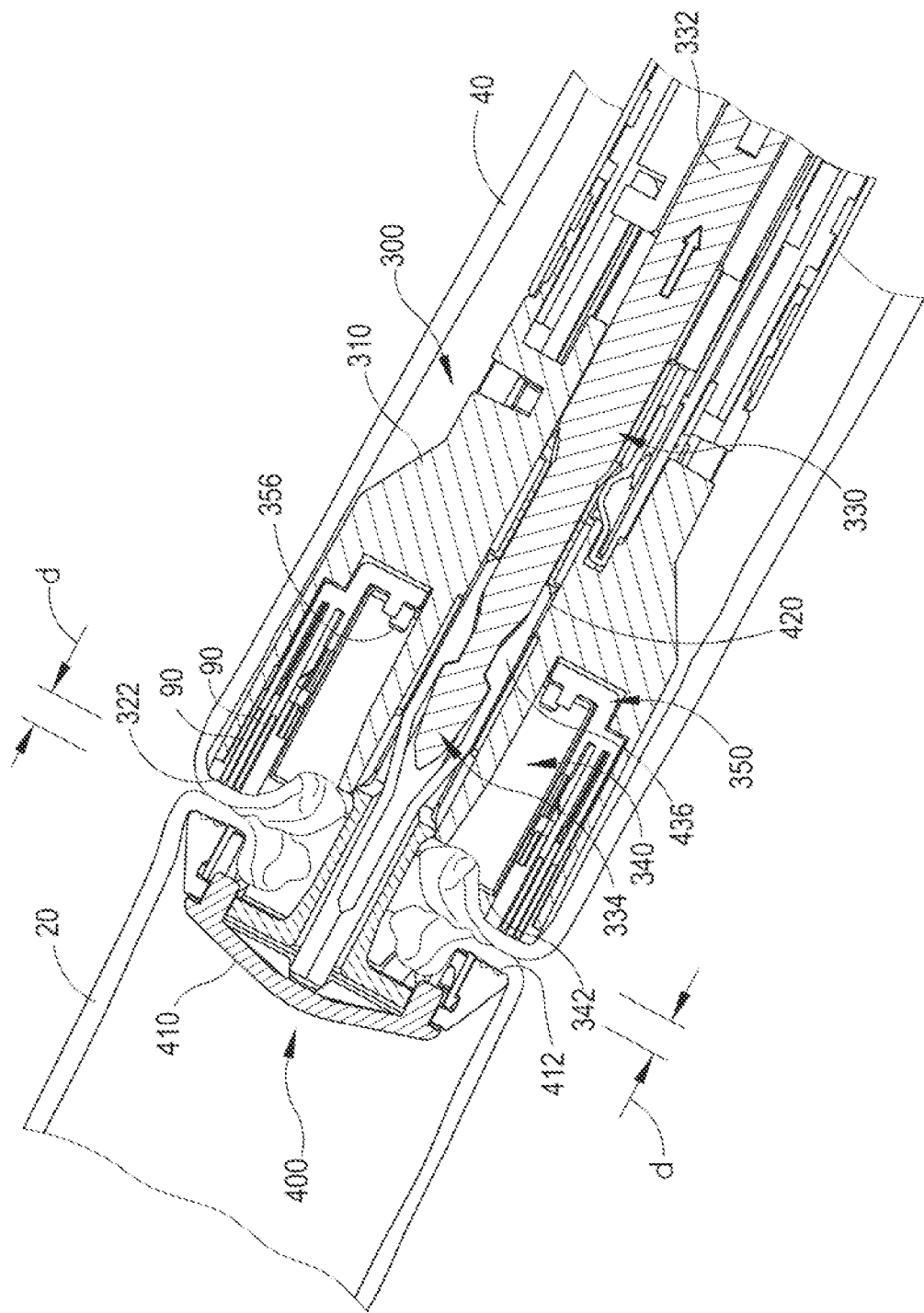
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
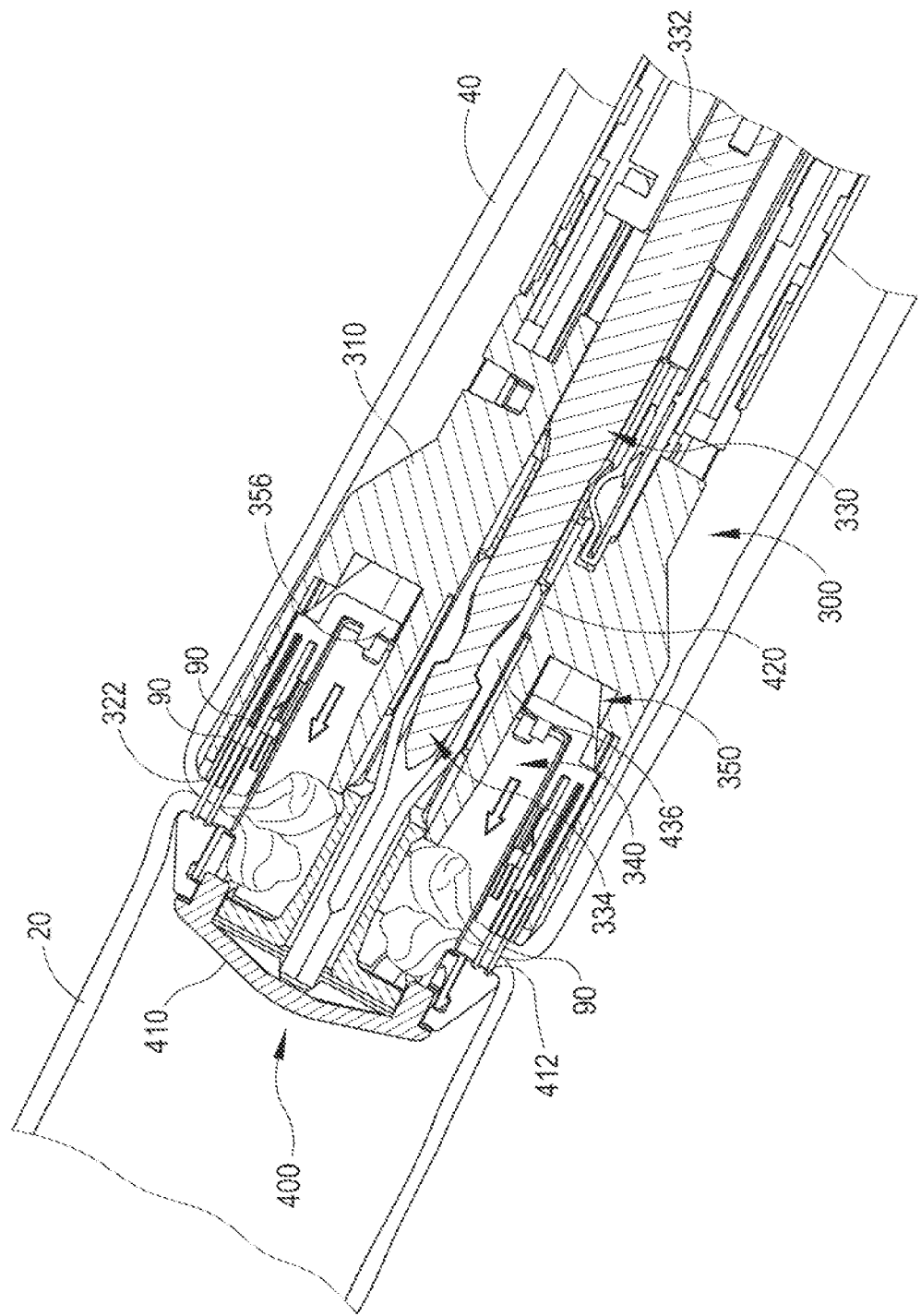
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (158) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
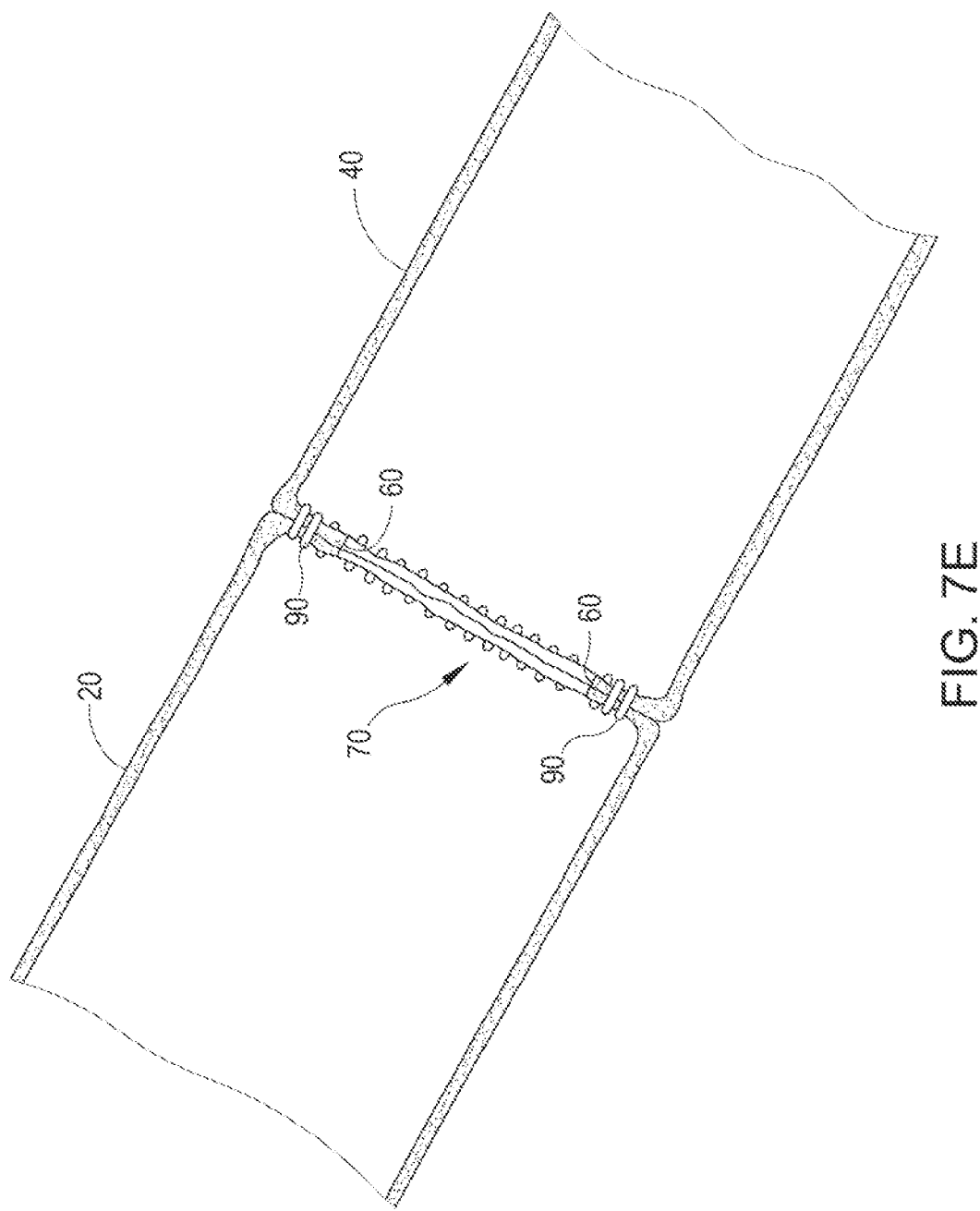
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

F. Exemplary User Interface Feature of Handle Assembly

Figure 8:
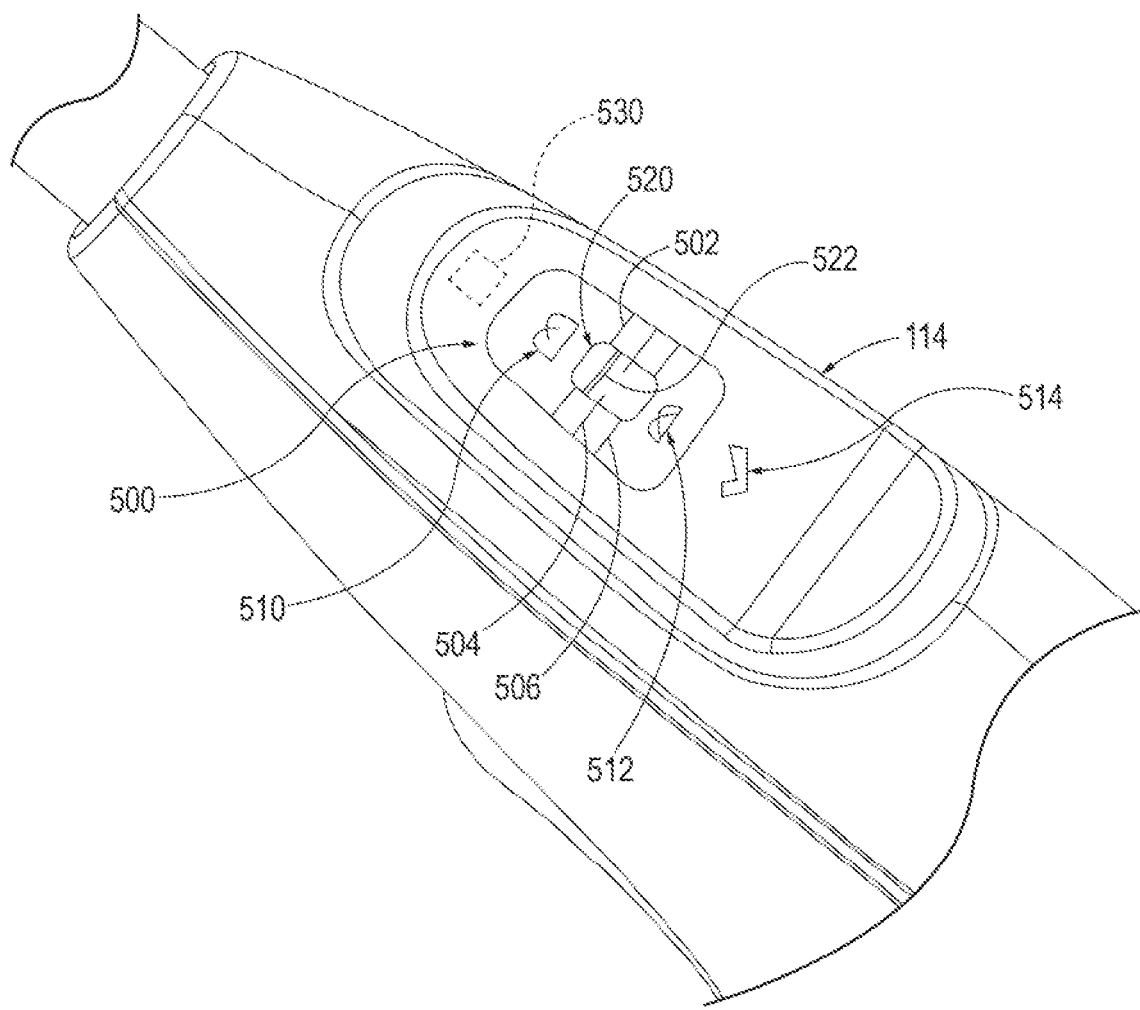
FIG. 8 depicts a perspective view of a user interface feature of the handle assembly of the circular stapler of FIG. 1.

As shown best in FIG. 8, handle assembly (100) of surgical stapling instrument (10) further includes a user interface feature (114) configured to provide the operator with visual feedback indicating the positioning of anvil (400) in relation to stapling head assembly (300) during a surgical procedure. The operator may thus observe user interface feature (114) while rotating knob (130) to confirm whether a suitable gap distance (d) between anvil (400) and stapling assembly (300) has been achieved.

User interface feature (114) of the present example includes a graphical indicator (500), which includes fixed linear indicia (502, 504, 506), graphical representations (510, 512) of staples, and a checkmark graphic (514). User interface feature (114) further defines a window (520) through which an indicator needle (522) may be viewed. In some variations, user interface feature (114) further includes a field (530) that may indicate a diameter associated with the size of stapling head assembly (300), the size of staples in stapling head assembly (300), the size of the gap defined between anvil (400) and stapling head assembly (300), and/or other information. By way of example only, field (530) may indicate a stapling head assembly (300) size of 23 mm, 25 mm, 29 mm, or 31 mm.

As the operator rotates knob (130) to adjust the longitudinal position of anvil (400) relative to stapling head assembly (300), the operator may observe the position of indicator needle (522) through window (520). Initially, indicator needle (522) may be positioned at or near the distal end of window (520). As anvil (400) continues to move proximally, indicator needle (522) will eventually move proximally relative to window (520). The operator may view the position of indicator needle (522) in relation to fixed linear indicia (502, 504, 506). The distal-most and proximal-most indicia (502, 506) may represent the boundaries of a "green zone," which is the acceptable range of distance between anvil (400) and stapling head assembly (300) for successful actuation of stapling head assembly (300). Thus, if indicator needle (522) is distal to distal-most indicia (502), the distance between anvil (400) and stapling head assembly (300) is too large; and if indicator needle (522) is proximal to proximal-most indicia (506), the distance between anvil (400) and stapling head assembly (300) is too small. Indicia (504) is longitudinally positioned between indicia (502, 506). Graphical representation (510) represents a relatively tall formed staple (e.g., suitable for use in relatively thick tissue); while graphical representation (512) represents a relatively short formed staple (e.g., suitable for use in relatively thin tissue). Graphical representations (510, 512) may thus facilitate the operator's decision, based on tissue observations or otherwise, on whether and how to achieve a desired formed staple height by selecting an appropriate corresponding spatial relationship between indicator needle (522) and indicia (502, 504, 506).

In the present example, window (520) is illuminated via a light emitting diode (LED) (not shown), further facilitating viewing of indicator needle (522) in window (520). In addition, checkmark graphic (514) is illuminated via another LED (not shown) when stapling head assembly (300) completes a stapling and cutting cycle. Thus, the operator may further rely on illumination of checkmark graphic (514) to confirm that the stapling and cutting cycle is complete, to thereby verify that it is safe to advance anvil (400) distally away from the anastomosis (70) to release the tissue and thereafter remove instrument (10) from the patient.

Circular surgical stapling instrument (10) may be further configured and operable in accordance with at least some of the teachings of U.S. Pub. No. 2017/0258471, issued as U.S. Pat. No. 10,709,452 on Jul. 14, 2020, incorporated by reference above.

II. Exemplary Circular Surgical Stapling Instrument Having Independently Controlled Closure, Stapling, and Cutting In some instances, it may be desirable to provide a version of circular surgical stapling instrument (10) that exhibits powered actuation of anvil (400) in addition to powered actuation of internal firing components of stapling head assembly (300). Furthermore, it may be desirable to provide such a version of instrument (10) with a plurality of actuators that enable independent, powered actuation of anvil (400), staple driver member (350), and knife member (340), such that the resulting closure, stapling, and cutting strokes performed by such an instrument may be controlled independently from one another in response to user input.

While the teachings below are disclosed in the context of circular surgical staplers, it will be appreciated that such teachings may be applied to other types of surgical staplers as well. By way of example only, such other staplers may include right-angle surgical staplers of the type disclosed in U.S. Pat. No. 10,045,780, entitled "Method of Applying Staples in Lower Anterior Bowel Resection," issued Aug. 14, 2018, the disclosure of which is incorporated by reference herein.

A. Overview of Circular Surgical Stapling Instrument Having Independently Controlled Actuators FIG. 9 shows an exemplary circular surgical stapling instrument (600) that exhibits a configuration and functionality of the kind described above. It will be understood that instrument (600) is similar to instrument (10) described above except as otherwise described below. Similar to instrument (10), instrument (600) generally includes a body assembly in the form of a handle assembly (610), a shaft assembly (630) extending distally from handle assembly (610), a stapling head assembly (640) disposed at a distal end of shaft assembly (630), and an anvil (650) configured to releasably couple with an actuatable closure member in the form of trocar (642) of stapling head assembly (640). Anvil (650) is selectively retractable and extendable by trocar (642) relative to stapling head assembly (640) for clamping tissue against a distally facing deck surface (644) thereof. Stapling head assembly (640) is selectively operable to eject staples distally into the clamped tissue and against anvil (650), and to cut the clamped tissue with a cylindraceous knife member (not shown) similar to knife member (340) described above. Accordingly, stapling head assembly (640) and anvil (650) cooperate to define an end effector stapling assembly operable to clamp, staple, and cut tissue in response to user inputs.

Handle assembly (610) includes a casing (612) defining a pistol grip (614), a user interface (616) disposed on an upper side of casing (612) adjacent to a distal end of casing (612), and a knob (618) rotatably disposed at a proximal end of casing (612). User interface (616) and knob (618) are similar to user interface (114) and knob (130) described above except as otherwise described below. Casing (612) of the present example includes an open-ended proximal cavity (not shown) configured to releasably receive and retain a battery pack (620) similar to battery pack (120) and operable to power a motor unit (660) (see FIG. 10) housed within casing (612).

Handle assembly (610) of the present example further includes a safety member (622), a closure trigger (624), and a firing trigger (626) each movable independently relative to pistol grip (614). Actuation of closure trigger (624) is configured to activate motor unit (660) to initiate actuation of a trocar actuator (662) (see FIG. 10) and thereby effect closure of anvil (650) relative to stapling head assembly (640) to clamp tissue therebetween. Actuation of firing trigger (626) is configured to activate motor unit (660) to initiate actuation of a staple actuator (664) and a knife actuator (666) (see FIG. 10) to thereby staple and cut the clamped tissue. As described in greater detail below in connection with FIG. 11, instrument (600) is configured to control actuation of staple actuator (664) and knife actuator (666) independently in response to a single actuation of firing trigger (626). In this manner, a precise timing of the cutting stroke initiation relative to the stapling stroke initiation may be achieved.

Safety member (622) of the present example is in the form of a projection, such as a pivotable trigger similar to safety trigger (140), and is configured to directly or indirectly engage closure trigger (624) and/or firing trigger (626) to selectively block actuation thereof. For instance, safety member (622) may be configured to block actuation of closure trigger (624) until instrument (600) detects that anvil (650) has been fully attached to trocar (642). Additionally, or in the alternative, safety member (622) may be configured to block actuation of firing trigger (626) until anvil (650) has assumed a predetermined longitudinal position relative to stapling head assembly (640) that defines a particular gap distance (d) therebetween (see FIG. 7C).

Figure 10:
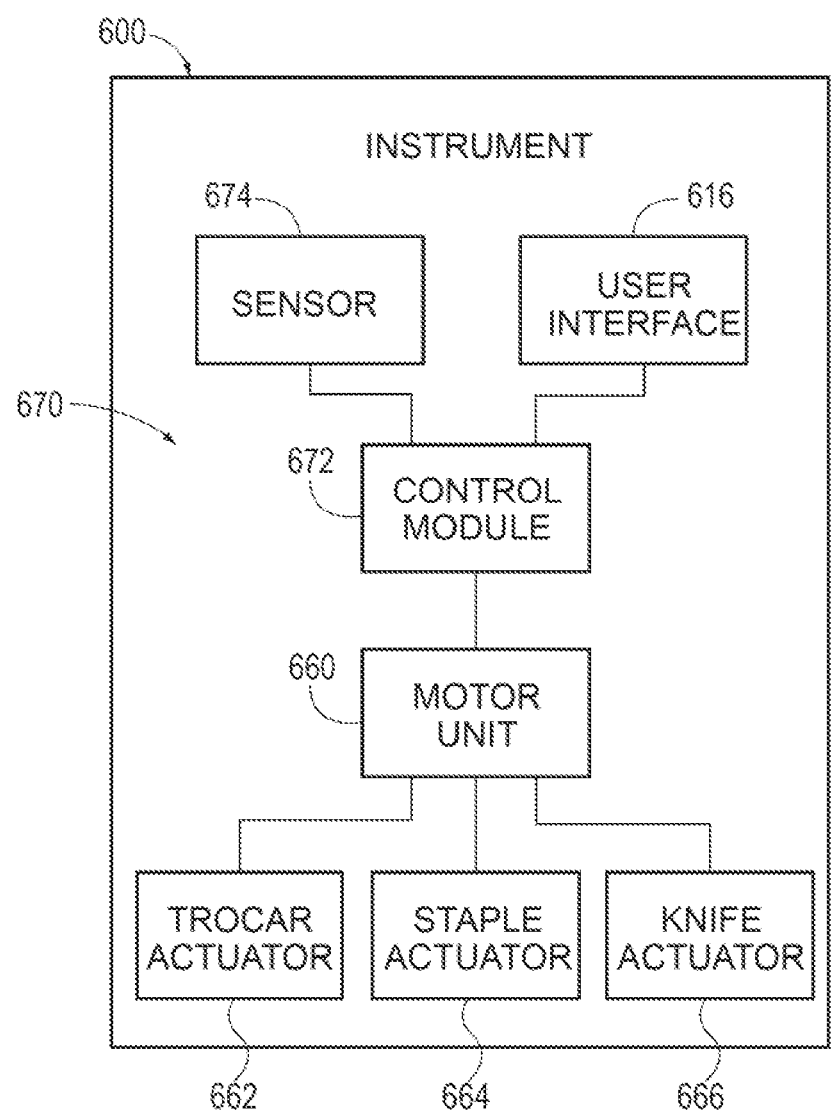
FIG. 10 depicts a schematic view of the circular stapler of FIG. 9, including a control system of the circular surgical stapler.

Actuators (662, 664, 666) of instrument (600), shown schematically in FIG. 10, are configured to operatively couple corresponding actuatable components of instrument (600) with motor unit (660). In particular, trocar actuator (662) operatively couples trocar (642) of stapling head assembly (640) with motor unit (660). Accordingly, trocar actuator (662) is configured to actuate trocar (642) and thus anvil (650) proximally and distally in response to activation of motor unit (660) when motor unit (660) is operatively engaged with trocar actuator (662). Trocar actuator (662) may include an elongate member similar to trocar actuation rod (220) combined with trocar actuation band assembly (230) of instrument (10), which is translatably disposed within shaft assembly (630).

Staple actuator (664) operatively couples a staple driver member (not shown) of stapling head assembly (640) with motor unit (660) independently of trocar actuator (662). Accordingly, staple actuator (664) is configured to actuate the staple driver member, and thus staples (not shown) housed within stapling head assembly (640), distally in response to activation of motor unit (660) when motor unit (660) is operatively engaged with staple actuator (664). Staple actuator (664) may include an elongate member similar to stapling head assembly driver (240) of instrument (10), which is translatably disposed within shaft assembly (630) independently of trocar actuator (662).

Knife actuator (666) operatively couples a cylindraceous knife member (not shown) of stapling head assembly (640) with motor unit (660) independently of trocar actuator (662) and staple actuator (664). Accordingly, knife actuator (666) is configured to actuate the knife member longitudinally in response to activation of motor unit (660) when motor unit (660) is operatively engaged with knife actuator (666). Knife actuator (666) may include an elongate member similar to stapling head assembly driver (240) of instrument (10), which is translatably disposed within shaft assembly (630) independently of trocar actuator (662) and staple actuator (664). In this manner, actuators (662, 664, 666) are configured to cooperate with motor unit (660) to provide independently actuated clamping of tissue, stapling of the tissue, and cutting of the tissue.

Knob (618) of handle assembly (610) of the present example is operatively coupled with trocar actuator (662) such that knob (618) is operable as an anvil closure bailout feature. In that regard, trocar actuator (662) is driven primarily by motor unit (660) but is also translatable longitudinally in response to rotation of knob (618), for example when motor unit (660) is deactivated or otherwise disengaged from trocar actuator (662). Accordingly, knob (618) may be rotated following partial or full proximal retraction of anvil (650) toward stapling head assembly (640) to thereby extend anvil (650) distally away from stapling head assembly (640), for example to release tissue captured therebetween. In such versions, knob (618) may be coupled with trocar actuator (662) via features similar to those described above in connection with knob (130) of instrument (10), including threaded portions (224, 226) of trocar actuation rod (220), for example. It will be understood, however, that knob (618) may be omitted from instrument (600) in some versions such that trocar actuator (662) is driven solely by motor unit (660).

Instrument (600) may be further configured and operable in accordance with at least some of the teachings of U.S. Pat. No. 9,445,816, entitled "Circular Stapler with Selectable Motorized and Manual Control," issued Sep. 20, 2016; U.S. Pat. No. 9,532,783, entitled "Circular Stapler with Select Motorized and Manual Control, Including a Control Ring," issued Jan. 3, 2017; U.S. Pat. No. 9,597,081, entitled "Motor Driven Rotary Input Circular Stapler with Modular End Effector," issued Mar. 21, 2017; U.S. Pat. No. 9,463,022, entitled "Motor Driven Rotary Input Circular Stapler with Lockable Flexible Shaft," issued Oct. 11, 2016; U.S. Pub. No. 2018/0368836, entitled "Surgical Stapler with Independently Actuated Drivers to Provide Varying Staple Heights," published Dec. 27, 2018, issued as U.S. Pat. No. 10,828,029 on Nov. 10, 2020; and/or any of the other patent references identified herein, the disclosures of which are incorporated by reference herein.

B. Exemplary Control System of Circular Surgical Stapling Instrument

As shown schematically in FIG. 10, instrument (600) further includes a control system (670) operable to control actuation of trocar actuator (662), staple actuator (664), and knife actuator (666) of instrument (600). Control system (670) includes a control module (672), motor unit (660), user interface (616), and a sensor (674) suitably arranged such that control module (672) communicates with each of motor unit (660), user interface (616), and sensor (674). Control module (672) includes a processor and is operable to store pre-programmed instrument control algorithms and receive input from user interface (616) and sensor (674). Based on these stored control algorithms and received input, control module (672) is configured to control motor unit (660) with pulse-width modulation (PWM) to drive actuation of trocar actuator (662), staple actuator (664), and knife actuator (666) independently from one another for clamping, stapling, and cutting tissue.

Motor unit (660) includes one or more motors and is operatively coupled with trocar actuator (662), staple actuator (664), and knife actuator (666). In some versions, motor unit (660) may comprise a single motor operatively coupled with and configured to drive all three actuators (662, 664, 666). In such versions, motor unit (660) may be coupled with actuators (662, 664, 666) via one or more power transmission assemblies (not shown), such as a gear assembly, various suitable types of which will be apparent to those of ordinary skill in the art in view of the teachings herein and in the incorporated references. In other versions, motor unit (660) may comprise three motors, each being dedicated to drive a respective one of actuators (662, 664, 666). In further versions, motor unit (660) may comprise two motors, a first motor of which is configured to drive trocar actuator (662) and a second motor of which is configured to drive staple actuator (664) and knife actuator (666) with assistance of a power transmission assembly. It will be understood that motor unit (660) may comprise various other quantities and arrangements of motors in other versions.

Sensor (674) is arranged within or otherwise coupled to stapling head assembly (640), shaft assembly (630), or handle assembly (610), and is operable to monitor one or more conditions of instrument (600) during use. For instance, sensor (674) may be configured to monitor translation of any one or more of actuators (662, 664, 666) and/or their adjoining components, such as trocar (642). In some such versions, sensor (674) may be mounted directly to any one of actuators (662, 664, 666) or an adjoining component thereof. In other such versions, sensor (674) may be fixedly mounted within stapling head assembly (640), shaft assembly (630), or handle assembly (610), such that actuators (662, 664, 666) and their adjoining components move relative to sensor (674).

In some versions, sensor (674) may be configured to detect secure attachment of anvil (650) to trocar (642), for example as disclosed in U.S. Pat. No. 10,307,157, incorporated by reference above; or in U.S. patent application Ser. No. 16/574,299, entitled "Anvil Retention and Release Features for Powered Circular Surgical Stapler," filed on Sep. 18, 2019, published as U.S. Pub. No. 2021/0077093 on Mar. 18, 2021, issued as U.S. Pat. No. 11,185,324 on Nov. 30, 2021, the disclosure of which is incorporated by reference herein. In other versions, sensor (674) may be configured to detect certain characteristics of the particular stapling head assembly (640) coupled with shaft assembly (630), such as a diameter of stapling head assembly (640) or a size of the staples (not shown) housed therein. In some such versions, sensor (674) may be configured to detect such characteristics of stapling head assembly (640) via radio-frequency identification (RFID) of electronic information stored within a tag element disposed on or within stapling head assembly (640), for example as disclosed in U.S. Provisional Pat. App. No. 62/868,457, entitled "Surgical Systems with Multiple RFID Tags," filed on Jun. 28, 2019, the disclosure of which is incorporated by reference herein.

Still in other versions, sensor (674) may be in direct communication with motor unit (660). For instance, sensor (674) may comprise a current sensor operable to monitor an electrical current drawn by motor unit (660), or an encoder operable to monitor a rotational output of motor unit (660). Moreover, while only one sensor (674) is illustrated in the diagram of FIG. 10, it will be understood that sensor (674) may comprise a plurality of sensors, where each individual sensor (674) is configured to monitor and communicate with control module (672) regarding a respective one or more conditions of instrument (600). Furthermore, it will be understood that sensor (674) may be in the form of a sensor assembly that includes various suitable types of sensors readily apparent to those of ordinary skill in the art in view of the teachings herein and not otherwise described herein.

User interface (616) is similar to user interface (114) described above, except that user interface (616) is further configured to receive and communicate user input to control module (672). In that regard, user interface (616) may include one or more buttons, dials, other actuatable elements, or displayed graphics that are selectable by a user to indicate certain information pertaining to a surgical procedure to be performed or to stapling head assembly (640). By way of example only, such information may include any of the following: a desired staple formation height; a corresponding gap between anvil (650) and stapling head assembly (640) to which anvil (650) should be actuated during closure; a type or nominal thickness of tissue being fired upon with instrument (600); and/or a diameter of stapling head assembly (640). Such information, in combination with information provided by sensor (674), may be used by control module (672) to adjust strokes and/or rates of actuation of actuators (662, 664, 666), and/or to adjust timing pauses between the powered actuations of actuators (662, 664, 666) to ensure optimal clamping, stapling, and cutting of tissue during a procedure, for example as described in greater detail below.

C. Exemplary Method for Controlling Circular Surgical Stapler

Figure 11:
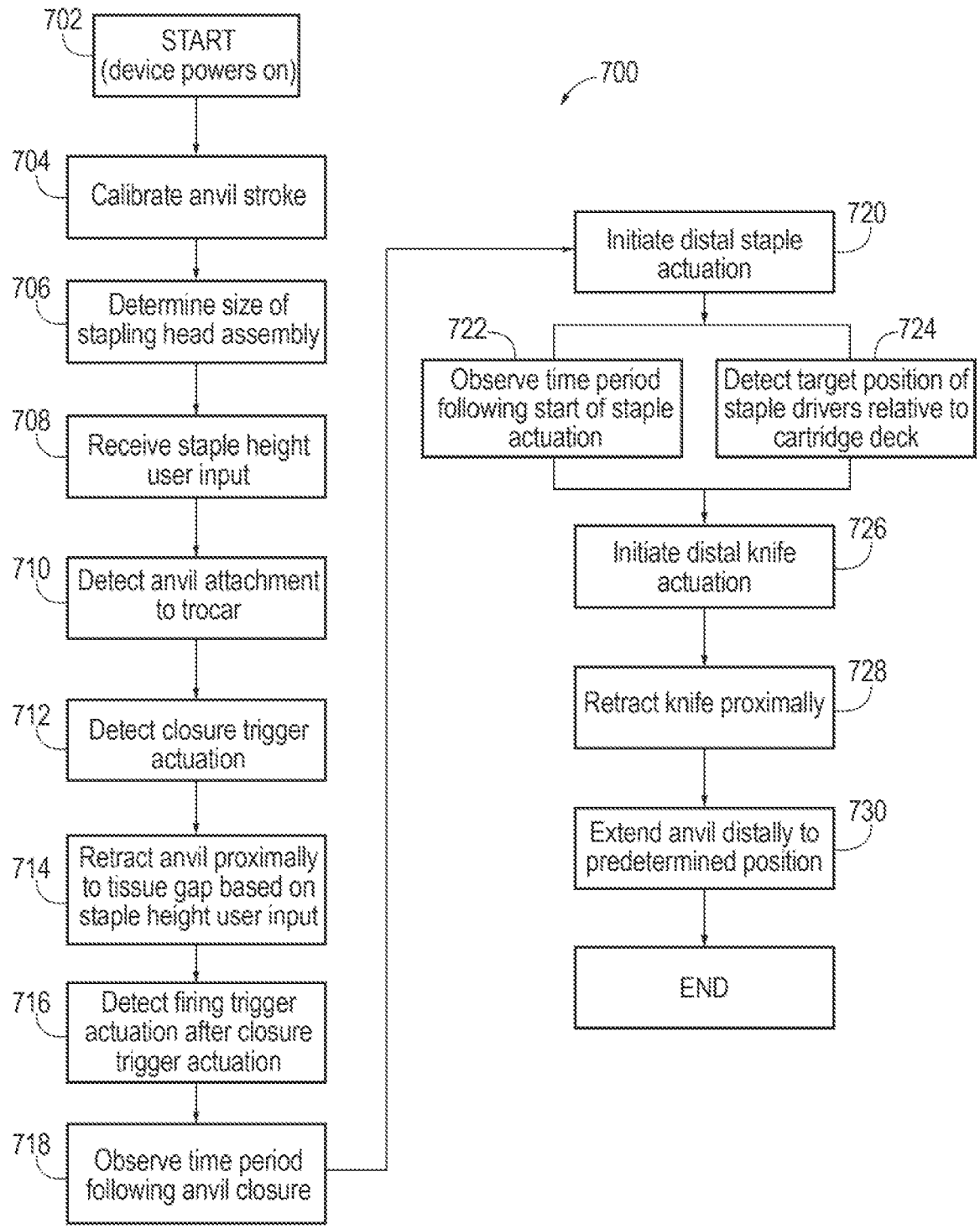
FIG. 11 depicts a diagrammatic view of an exemplary method for controlling the circular surgical stapler of FIG. 9 via the control system of FIG. 10.

FIG. 11 shows an exemplary method (700) for controlling circular surgical stapling instrument (600) via control system (670) shown in FIG. 10. At step (702), instrument (600)

powers on in response to being energized by battery pack (620), for example when battery pack (620) is fully inserted into the proximal end of handle assembly (610) after instrument (600) is removed from product packaging. Upon removal from the packaging, anvil (650) is already secured to trocar (642) and is in a fully open state, and a staple retainer (646) (see FIG. 14) is secured to deck surface (644).

After instrument (600) powers on in the present example, control module (672) enters an anvil stroke calibration mode at step (704), which may occur automatically or in response to a user input, for example provided via user interface (616). In this calibration mode, control module (672) activates motor unit (660) to drive trocar actuator (662) to retract trocar (642) proximally and thereby close anvil (650) against the staple retainer (646), or alternatively against deck surface (644) in the event that the staple retainer (646) has been removed. Control module (672) may detect that anvil (650) has reached a closed position by detecting via sensor (674) an increase in the electrical current load of motor unit (660) upon contact of anvil (650) with the staple retainer (646) or deck surface (644). Control module (672) observes the stroke (i.e., longitudinal displacement) of anvil (650) during this retraction process and compares it to an expected stroke of anvil (650). Based on this comparison and any differences observed between the two stroke values, control module (672) then calibrates an actuation algorithm that is executed to activate motor unit (660) to actuate trocar actuator (662), and thereby ensure precise actuations of anvil (650) thereafter during a surgical procedure. In addition, or in the alternative, calibration of the anvil stroke may be performed by control module (672) in real time during a surgical procedure when anvil (650) is being retracted to clamp tissue. Such calibration of the anvil stroke is described in further detail below. It will be understood that the strokes of one or more other actuatable members of instrument (600) may be calibrated in a similar manner before or during a surgical procedure, and also that the calibration of the anvil closure stroke may be applied by control module (672) to also calibrate the stapling stroke and/or the cutting stroke of instrument (600).

At step (706), control module (672) determines a diameter of stapling head assembly (640). As described above, stapling head assembly (640) may be releasably attached to shaft assembly (630) such that stapling head assemblies (640) of various diameters may be interchangeably coupled with the distal end of shaft assembly (630) depending on a lumen size of the tissue structure being operated on with instrument (600). Control module (672) is configured to make this size determination based on user input provided via user interface (616) and/or information provided by sensor (674), for instance when sensor (674) is configured to detect the size of stapling head assembly (640) in the manner described above.

At step (708), control module (672) receives from user interface (616) input that indicates a desired height of staples to be formed in tissue, as selected by the operator via user interface (616). Control module (672) equates this staple height to a corresponding gap distance (d) (see FIG. 7C) to be established between anvil (650) and deck surface (644) of stapling head assembly (640) at a closed position of anvil (650), in order to achieve the selected staple height.

While steps (704, 706, 708) are shown in FIG. 11 as being performed in a particular order, it will be appreciated that these steps (704, 706, 708) may be performed in a variety of orders relative to one another following the powering on of instrument (600) in step (702) and before the actuation of staple actuator (664) described below.

Following completion of steps (704, 706, 708), the operator detaches anvil (650) from trocar (642) and proceeds to position anvil (650) within a first tubular tissue structure of a patient and separately position stapling head assembly (640) within a second tubular tissue structure of the patient. The operator then attaches anvil (650) to trocar (642) within the patient, for example as shown in FIGS. 7A-7B described above, at which point control module (672) detects at step (710) that the attachment has been made. Such detection may be made by sensor (674), which communicates a corresponding signal to control module (672).

At step (712), control module (672) detects that closure trigger (624) has been actuated by the operator. Control module (672) then proceeds to step (714) and directs motor unit (660) to drive trocar actuator (662) to actuate trocar (642) proximally and thereby retract anvil (650) to a closed position at which the selected staple height and corresponding gap distance (d) are achieved. In some versions, control module (672) may be configured to initiate retraction of trocar (642) and anvil (650) only in response to an actuation of closure trigger (624) that occurs after attachment of anvil (650) to trocar (642) has been detected at step (710). The operator may monitor the retraction of anvil (650) toward its closed position via visual indicia and/or displayed graphics of user interface (616).

Additionally, in some versions, control module (672) may control motor unit (660) to retract anvil (650) proximally through the anvil closure stroke in two sequential stages. For instance, control module (672) may direct motor unit (660) to retract anvil (650) through a first portion of the anvil closure stroke, at which point control module (672) pauses activation of motor unit (660) for a predetermined period of time (e.g., several seconds). At the end of this wait period, control module (672) reactivates motor unit (660) to continue retracting anvil (650) through the remaining portion of the anvil closure stroke to its closed position. Inclusion of such a pause in the retraction of anvil (650) may enable the tissue being compressed between anvil (650) and deck surface (644) to at least partially settle (or "creep"). Advantageously, this settling of tissue yields a reduction of the axial extension load on trocar (642) and the resulting electrical current load of motor unit (660) as anvil (650) advances proximally to its fully closed position defined by the target staple height input provided by the user in step (708).

At step (716), control module (672) detects that firing trigger (626) has been actuated by the operator following completion of the anvil closure stroke. In the present example, in response to detecting this actuation, control module (672) observes completion of a predetermined period of time measured from completion of the anvil closure stroke, during which staple actuator (664) and knife actuator (666) remain stationary. This wait period after anvil closure enables the clamped tissue to settle (or "creep") into its fully compressed state before stapling head assembly (640) is fired, thus reducing the axial loads on staple actuator (664) and knife actuator (666), and the resulting current loads of motor unit (660), during the respective stapling and cutting sequences. It will be understood that this wait period may be omitted in some versions.

Upon completion of the wait period denoted in step (718), control module (672) initiates distal actuation of the staple driver member (not shown) at step (720) to begin stapling the clamped tissue. In particular, control module (672) activates motor unit (660) to engage and drive staple actuator (664) to actuate the staple driver member distally through stapling head assembly (640) and thereby drive staples into tissue and against anvil (650), for example similar to the manner shown in FIG. 7D. Upon initiating actuation of staple actuator (664), control module (672) at step (722) observes another predetermined period of time during which motor unit (660) continues to drive staple actuator (664) through the stapling stroke. Simultaneously, at step (724) control module (672) communicates with sensor (674) to detect when the staple driver member reaches a predetermined longitudinal position within stapling head assembly (640). Such a position may correspond to the point at which individual staple drivers (not shown), similar to staple drivers (352) described above, reach deck surface (644) such that the staples are at least partially formed within the clamped tissue. This process is described in further detail below in connection with FIGS. 17-19.

In response to detecting completion of the predetermined time period of step (722) and/or detecting at step (724) that the staple driver member has reached the predetermined longitudinal position, control module (672) then initiates distal actuation of the knife member (not shown) at step (726) to begin cutting the tissue. In particular, control module (672) activates motor unit (660) to engage and drive knife actuator (666) to actuate the knife member distally through stapling head assembly (640) and thereby cut the tissue, for example similar to the manner shown in FIG. 7D.

As noted above, delaying initiation of the cutting stroke relative to initiation of the stapling stroke, as enabled by independent actuation of staple and knife actuators (662, 664, 666), ensures at least partial formation of staples within the tissue before tissue cutting commences. Advantageously, this approach enables the staples to anchor within the clamped tissue before cutting, and thereby prevent lateral shifting of the tissue and resulting malformation of the staples when the knife member is driven distally.

The end of the distal cutting stroke of the knife member may correspond to a point at which the knife member breaks a washer (not shown) within anvil (650) similar to washer (417) described above. Upon completion of the distal cutting stroke, control module (672) at step (728) directs motor unit (660) to retract the knife member proximally back into stapling head assembly (640). In some versions, knife member distal extension and subsequent proximal retraction may be achieved by powering motor unit (660) through a continuous, uniform range of motion, for example as disclosed in U.S. Pub. No. 2017/0258471 incorporated by reference above. In other versions, control module (672) may be programmed to communicate with sensor (674) to detect completion of the distal cutting stroke, and thereafter specifically direct motor unit (660) to drive knife actuator (666) in an alternative manner to retract the knife member proximally. In any of such versions, sensor (674) may comprise an encoder configured to monitor a rotational output of motor unit (660).

Simultaneously with or subsequently to knife retraction step (728), control module (672) at step (730) directs motor unit (660) to drive trocar actuator (662) distally to thereby extend anvil (650) distally to a predetermined position relative to deck surface (644) of stapling head assembly (640). This distal extension enables the stapled tissue to be released from between anvil (650) and stapling head assembly (640) so that instrument (600) may be withdrawn from the patient while anvil (650) remains attached to trocar (642).

III. Exemplary Method for Calibrating Actuation Strokes of Circular Surgical Stapler As described above, it may be desirable to calibrate the longitudinal actuations (or "strokes") of trocar actuator (662), staple actuator (664), and knife actuator (666) before or during a surgical procedure. This ensures that the actual longitudinal displacements of anvil (650), the staple driver member (not shown), and the knife member (not shown) are consistent with corresponding expected longitudinal displacements anticipated by control module (672) based on a given rotational output of motor unit (660). As described below, proper calibration of these strokes enables circular stapler (600) to provide precise clamping, stapling, and cutting of patient tissue.

Control module (672) of the present example is configured to store and execute a closure member actuation algorithm to longitudinally actuate trocar actuator (662) (and thus trocar (642) and anvil (650)) to clamp tissue; a staple driver member actuation algorithm to longitudinally actuate staple actuator (664) (and thus staple driver member) to staple tissue; and a knife member actuation algorithm to longitudinally actuate knife actuator (666) (and thus knife member) to cut tissue. Each of these actuation algorithms stored by control module (672) comprises a correlation between a given rotational output of motor unit (660) and an expected longitudinal displacement of the corresponding actuated member of stapler (600) effected by that particular rotational output. As described above, the rotational output of motor unit (660) may be monitored by an encoder operatively coupled with motor unit (660) and in communication with control module (672). As described below, the longitudinal strokes of actuators (662, 664, 666) may be calibrated by adjusting the corresponding actuation algorithms stored by control module (672).

A. Exemplary Actuation Stroke Calibration Method

Figure 12:
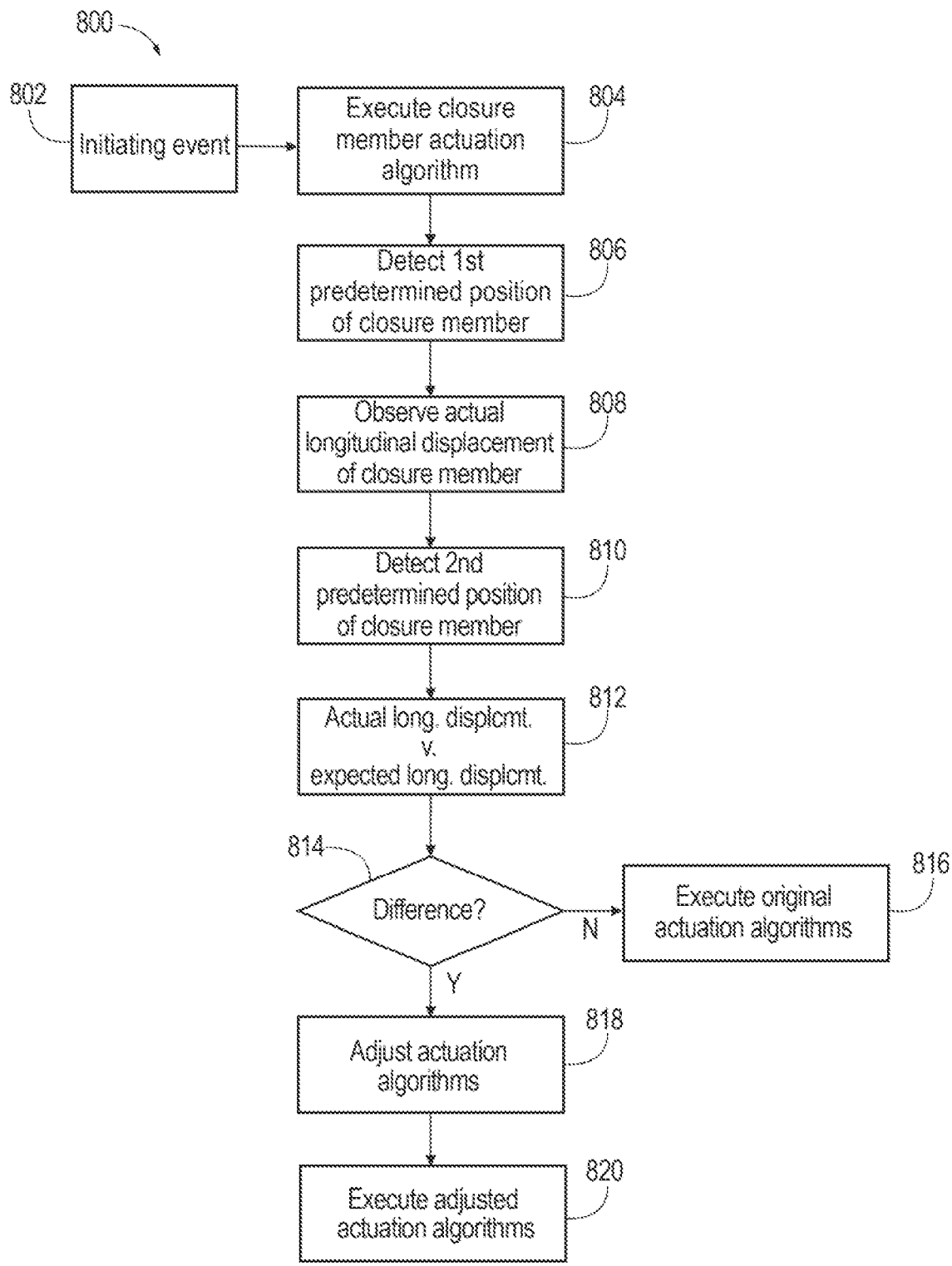
FIG. 12 depicts a diagrammatic view of an exemplary method for calibrating actuation strokes of moveable members of the circular stapler of FIG. 9 by adjusting actuation algorithms executed by the control system of FIG. 10.

FIG. 12 shows an exemplary method for calibrating the stroke of at least trocar actuator (662) (and the connected trocar (642) and anvil (650)) by adjusting the closure member actuation algorithm to redefine the correlation between rotational output of motor unit (660) and longitudinal displacement of trocar actuator (662). As described above in connection with step (704) of operation method (700) shown in FIG. 11, this calibration process may be performed upon an initial unpackaging of circular stapler (600) prior to a surgical procedure. Additionally, or in the alternative, this calibration process may be performed in real-time during a surgical procedure, as described in greater detail below. Furthermore, as described below, the adjustment of the closure member actuation algorithm can be used by control module (672) to also adjust the staple driver member actuation algorithm and the knife member actuation algorithm, to thereby calibrate the staple driver member stroke and the knife member stroke. In some versions, however, steps similar to those shown in FIG. 12 may be performed by control module (672) to adjust the staple driver member actuation algorithm and the knife member actuation algorithm independently of the closure member actuation algorithm.

As shown in FIG. 12, calibration method (800) begins at step (802) with an initiating event, which may be an initial mating of battery pack (620) with handle assembly (610) after device unpackaging, or alternatively an actuation of closure trigger (624) following attachment of anvil (650) to trocar (642) during a surgical procedure. In response to the initiating event (802), control module (672) executes the stored closure member actuation algorithm at step (804) to activate motor unit (660) to actuate trocar actuator (662) proximally to transition anvil (650) toward a closed state. Prior to or during execution of the closure member actuation algorithm, control module (672) determines at step (806) that a monitored one of trocar actuator (662), trocar (642), or anvil (650) (each a "closure member" herein) is in a first predetermined position, for example via detection by sensor (674) in the form of a position sensor. By way of example only, the first predetermined position may correspond to anvil (650) in a fully open state ($X_O$) as shown in FIG. 13A, in which anvil (650) is in a distal-most position relative to deck surface (644). In other examples, the first predetermined position may correspond to anvil (650) in a partially closed state. Motor unit (660) continues to retract trocar actuator (662) proximally while control module (672) observes an actual longitudinal displacement of one of the monitored closure member (642, 650, 662) at step (808), for example via sensor (674) in the form of a sensor. It will be understood that trocar actuator (662), trocar (642), and anvil (650) of the present example translate together such that their longitudinal displacements are the same for a given output of motor unit (660).

Figure 13:
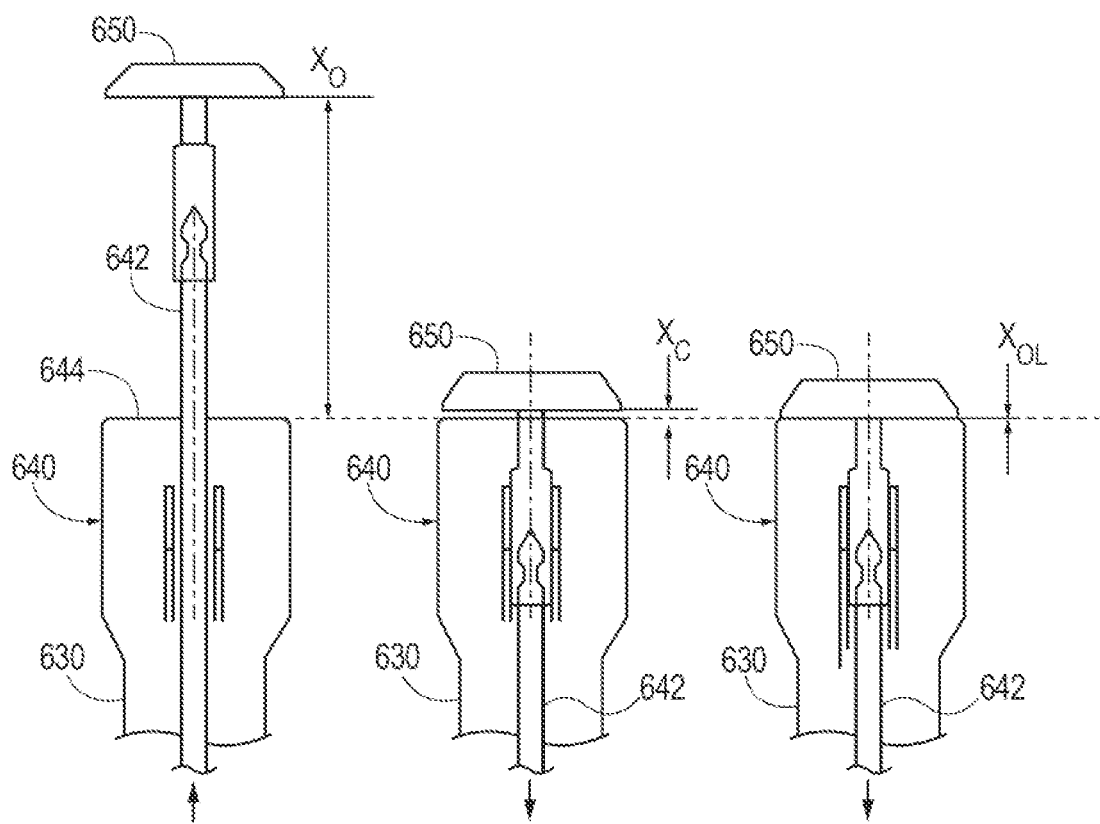
FIG. 13A depicts a schematic side sectional view of the stapling head assembly and anvil of the circular surgical stapler of FIG. 9, showing the anvil in a fully open position relative to the stapling head assembly.
FIG. 13B depicts a schematic side cross-sectional view of the stapling head assembly and anvil of the circular surgical stapler of FIG. 9, showing the anvil in a partially closed position relative to the stapling head assembly.
FIG. 13C depicts a schematic side cross-sectional view of the stapling head assembly and anvil of the circular surgical stapler of FIG. 9, showing the anvil in a fully closed position against the stapling head assembly.
Figure 14:
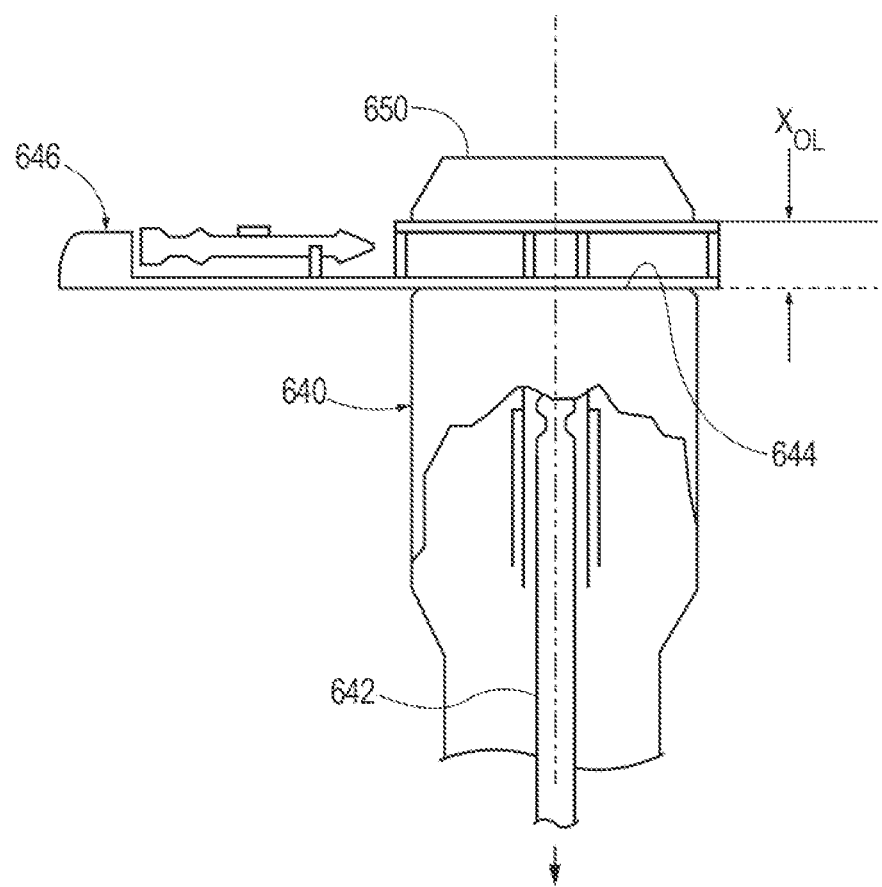
FIG. 14 depicts a schematic side cross-sectional view of the staple assembly and anvil of the circular surgical stapler of FIG. 9, showing the anvil in a fully closed position against a staple retainer of the stapling head assembly.

At step (810), control module (672) determines that the monitored closure member (642, 650, 662) has reached a second predetermined position located proximal to the first predetermined position. By way of example only, the second predetermined position may correspond to anvil (650) in an initially closed state in which anvil (650) confronts but is not drawn against deck surface (644), for example as shown by position ($X_C$) in FIG. 13B. In other versions, the second predetermined position may correspond to anvil (650) in a fully closed and overloaded state in which anvil (650) is compressed against deck surface (644) or another structure. For instance, FIG. 13C shows anvil (650) in an exemplary fully closed and overloaded state ($X_{OL}$) in which anvil (650) is drawn against deck surface (644). FIG. 14 shows another exemplary fully closed and overloaded state ($X_{OL}$) of anvil (650) in which anvil (650) is drawn against a staple retainer (646) prior to the removal of retainer (646) from stapling head assembly (640) after unpackaging of circular stapler (600). In that regard, it will be understood that FIGS. 13A-14 illustrate exemplary positions of anvil (650) in the absence of tissue, for example prior to performance of a surgical procedure on a patient. As described above, however, calibration method (800) may also be performed in real-time during a surgical procedure while anvil (650) is being closed on patient tissue.

In any such versions where the second predetermined position of the monitored closure member (642, 650, 662) corresponds to a state in which anvil (650) is drawn against another structure (e.g., deck surface (644), staple retainer (646), or patient tissue), reaching of the second predetermined position may be identified by control module (672) based on an observed increase in load on the closure system components. This load may be detected in the form of a longitudinal force exerted on trocar actuator (662) (and thus also anvil (650) and trocar (642)), or an electrical current drawn by motor unit (660) while actuating trocar actuator (662). In that regard, it will be understood that closure of anvil (650) against a structure induces a longitudinal extension force in anvil (650), trocar (642), and trocar actuator (662) that makes further proximal retraction of these closure components by motor unit (660) more difficult, thus increasing the electrical current load of motor unit (660). This increase in closure load may be detected by one or more sensors in the form of a current sensor or a force sensor that communicate with control module (672).

Upon determining that the monitored closure member (642, 650, 662) has reached the second predetermined position, control module (672) proceeds to step (812) and compares the actual longitudinal displacement of the monitored closure member (642, 650, 662) observed by control module (672), via one or more sensors (674), to an expected longitudinal displacement stored by control module (672). Control module (672) evaluates at step (814) whether there is a difference between the observed actual longitudinal displacement and the stored expected longitudinal displacement. If the two longitudinal displacement values are equal or within a predetermined acceptable range of one another such that there is no significant difference, control module (672) proceeds to step (816) to execute the original stored actual algorithms in response to user actuations of closure trigger (624) and firing trigger (626), for example as outlined above in the steps of method (700).

Alternatively, if control module (672) determines that there is a significant difference between the actual and expected longitudinal displacements, control module (672) proceeds to step (818) to adjust at least the closure member actuation algorithm based on the determined difference. More specifically, in the present example, control module (672) redefines the stored correlation between a given rotational output of motor unit (660) and the corresponding expected longitudinal displacement of the monitored closure member (642, 650, 662). The newly defined correlation relates the observed actual longitudinal displacement of the closure member (642, 650, 662) with the rotational output of motor unit (660) during the observed longitudinal displacement of the closure member (642, 650, 662). This rotational output of the new correlation may be the same as or different than the rotational output of the original correlation.

In some versions, the staple member actuation algorithm and the knife member actuation algorithm may be adjusted in a similar manner based on the same difference value determined by control module (672) in connection with actuation of the monitored closure member (642, 650, 662). It will be understood that calibration of all three actuation algorithms ensures precise longitudinal actuation of anvil (650), the staple driver member, and the knife member of stapler (600). After adjusting the closure member actuation algorithm, and optionally also the staple driver member and knife member actuation algorithms, control module (672) proceeds to step (820) to execute the adjusted actual algorithms in response to user actuations of closure trigger (624) and firing trigger (626), for example as outlined above in the steps of method (700).

As noted above, it will be appreciated that the closure member calibration process (800) of FIG. 12 may be performed prior to a surgical procedure such that the longitudinal stroke of trocar actuator (662) (and trocar (642) and anvil (650)) is properly calibrated before clamping tissue. Additionally, or in the alternative, calibration process (800) may be performed one or more times during a surgical procedure on tissue to ensure that the longitudinal stroke of trocar actuator (662), and optionally also the longitudinal strokes of staple actuator (664) and knife actuator (666), remain properly calibrated throughout use.

Figure 15:
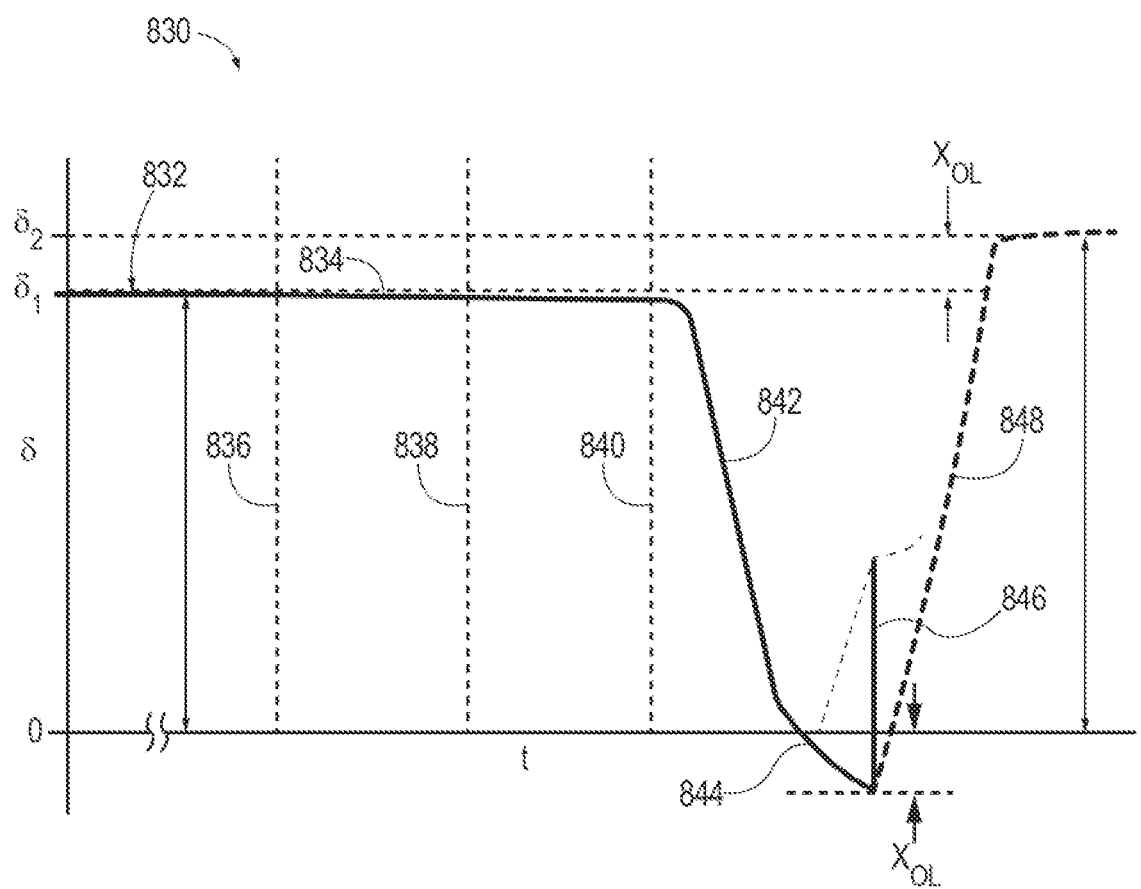
FIG. 15 depicts a line graph showing longitudinal displacement of the anvil of the circular surgical stapler of FIG. 9 from a fully open position to a fully closed position and back to the fully open position, showing calibration of the anvil stroke after closure and before reopening.

FIG. 15 depicts a line graph (830) showing an exemplary calibration of the longitudinal stroke of trocar actuator (662) (and thus trocar (642) and anvil (650)) per method (800) described above. The X-axis of graph (830) represents time and the Y-axis of graph (830) represents a distal displacement ($\delta$) of trocar actuator (662) relative to a proximal-most position (i.e., a distal displacement of anvil (650) relative to deck surface (644)), as interpreted by control module (672). A first horizontal portion (834) of the illustrated curve (832) indicates trocar actuator (662) in a dully extended position at displacement ($\delta_1$) before calibration of the longitudinal stroke. In the present example, trocar actuator (662) remains in the fully extended position throughout initial events including removal of stapler (600) from package as indicated by vertical dashed line (836), attachment of battery pack (620) to handle assembly (610) as indicated by vertical dashed line (838), and attachment of anvil (650) to trocar (642) as indicated by vertical dashed line (840).

First descending portion (842) of curve (832) represents initial proximal retraction of trocar actuator (662) to transition anvil (650) from the fully open position to a partially closed position at a first, rapid actuation rate. Second descending portion (844) of curve (832) represents final proximal retraction of trocar actuator (662) to transition anvil (650) from the partially closed state to a fully closed state at a second, slower actuation rate. Upon anvil (650) reaching the fully closed and overloaded state ($X_{OL}$), motor unit (660) experiences a sudden increase in electrical current load, as represented by vertical line (846). Control module (672) detects this increase in electrical current load via sensor (674) and thereby determines that anvil (650) has reached the fully closed state. Control module (672) then proceeds to compare the actual observed longitudinal displacement of trocar actuator (662) observed during proximal retraction with an expected longitudinal displacement, and control module (672) determines a difference between the two values.

In the present example, control module (672) adjusts the closure member actuation algorithm based on the determined difference to thereby re-"zero" the proximal end of longitudinal stroke of trocar actuator (662), for example via the steps described above in connection with method (800). Subsequently, control module (672) executes the adjusted closure member actuation algorithm to extend trocar actuator (662) distally to a fully extended state and thereby return anvil (650) to a fully open state ($X_O$), as represented by ascending curve portion (848). Because the longitudinal stroke is now calibrated with a proper "zero" point, the fully extended state of trocar actuator (662) and corresponding fully open state ($X_O$) of anvil (650) registers as a new, greater displacement ($\delta_2$) on the displacement scale applied by control module (672). As shown on graph (830), the difference between the original displacement value ($\delta_1$) and the adjusted displacement value ($\delta_2$) correlated by control module (672) with a fully extended state of trocar actuator (662) (i.e., the fully open state ($X_O$) of anvil (650)) is equal to the displacement amount by which the "zero" point of trocar actuator (662) is adjusted by control module (672).

Execution of the adjusted closure member actuation algorithm for subsequent actuations of trocar actuator (662) ensures accurate positioning of anvil (650) relative to deck surface (644), and thus precise clamping of tissue per user inputs. As described above, control module (672) may apply this calibration of the closure member actuation algorithm to also calibrate the staple member actuation algorithm and the knife member actuation algorithm, thus providing precise stapling and cutting of tissue as well.

B. Exemplary Actuation of Stapling Head Assembly per User-Specified Tissue Gap

As described above, user interface (616) of circular surgical stapler (600) is configured to receive and communicate user input to control module (672). As shown in FIG. 16, a visual display (680) of user interface (616) (which may be in the form of a window similar to window (520) in other versions) includes a distal linear indicia (682) and a proximal linear indicia (684). Linear indicia (682, 684) define the boundaries of an acceptable range (referred to as a "green zone") of a tissue gap defined longitudinally between anvil (650) and deck surface (644) of stapling head assembly (640) to enable proper formation of staples fired into tissue. Distal linear indicia (682) indicates a large tissue gap setting that provides anvil (650) in a distal, "tall" closed position ($A_T$) to define a large tissue gap ($\delta_{AT}$) between anvil (650) and deck surface (644), as shown in FIG. 17A. Proximal linear indicia (684) indicates a small tissue gap setting that provides anvil (650) in a proximal, "low" closed position ($A_L$) to define a small tissue gap ($\delta_{AT}$) between anvil (650) and deck surface (644), as shown in FIG. 17B. As indicated by symbols (686, 688) of user interface (616), the large tissue gap setting results in formation of staples (692) with a taller formed height (e.g., for thicker tissues), and the small tissue gap setting results in formation of staples (692) with a shorter formed height (e.g., for thinner tissues).

User interface (616) includes one or more selectable input features that enable a user to specify a desired tissue tap setting for anvil (650) in the closed position, which is then communicated by user interface (616) to control module (672). As described above in connection with step (714) of method (700), control module (672) is configured to control motor unit (660) to retract trocar actuator (662) proximally until anvil (650) achieves the target tissue gap setting specified via the user input. This may be confirmed by control module (672) via communication with sensor (674) in the form of a position sensor, which may be located in stapling head assembly, for example. As described above in connection with FIGS. 12-15, the longitudinal stroke of trocar actuator (662) may be calibrated before and/or during closure of anvil (650) on patient tissue such that the actual tissue gap ($\delta$) defined between anvil (650) and deck surface (644) is equal to the target tissue gap ($\delta$) specified by the user via user interface (616).

The target tissue gap ($\delta$) input by user via user interface (616) may be referenced by control module (672) in controlling other operational aspects of stapler (600) as well. For instance, in addition to controlling the longitudinal displacement of trocar actuator (662) during the anvil closure stroke, control module (672) may also control the longitudinal displacement of staple actuator (664) during the stapling stroke and the longitudinal displacement of knife actuator (666) during the cutting stroke based on the tissue gap user input. In particular, control module (672) may tailor the longitudinal displacements of each actuator (662, 664, 666) to ensure that actuators (662, 664, 666) are actuated longitudinally by the appropriate amount to provide a full stapling stroke and a full cutting stroke without under-actuation or over-actuation relative to the target tissue gap. In that regard, it will be appreciated that calibration of the longitudinal strokes of staple actuator (664) and knife actuator (666) may be desirable to ensure that staple actuator (664) and knife actuator (666) are actuated by the appropriate amount during a surgical procedure. As described above, the corresponding staple member actuation algorithm and knife member actuation algorithm may be adjusted appropriately based on the adjustments made to the closure member actuation algorithm via calibration method (800). Alternatively, the staple member actuation algorithm and knife member actuation algorithm may be adjusted independently of the closure member actuation algorithm, for example via steps similar to those of method (800).

The target tissue gap user input may also be reference by control module (672) to control a rate of actuation of one or more actuators (662, 664, 666). For instance, control module (672) may decrease the actuation rates of one or more actuators (662, 664, 666) for larger tissue gaps and increase the actuation rates of one or more actuators (662, 664, 666) for smaller tissue gaps. In that regard, it will be appreciated that larger tissues gaps are often selected to accommodate thicker tissues, which can induce higher electrical current loads for motor unit (660) during stapling and cutting. Reducing the actuation rate of staple actuator (664) and knife actuator (666) for thicker tissues can thus help to maintain the electrical current load of motor unit (660) below a desired threshold.

IV. Exemplary Method of Controlling Knife Member Actuation Relative to Staple Driver Member Actuation As described above in connection with steps (720-726) of method (700), control module (672) is configured to control motor unit (660) to actuate staple actuator (664) and knife actuator (666) independently such that the knife member is actuated distally only once the staples (692) driven by the staple driver member are at least partially formed within the tissue by anvil (650). More specifically, control module (672) communicates with sensor (674) to detect when staple actuator (664), the staple driver member (not shown), or individual staple drivers (690) (see FIG. 18) of the staple driver member reaches a predetermined longitudinal position in which the upper end of staple drivers (690) and crowns (694) of staples (692) are positioned at deck surface (644) such that staple legs (696) are partially deformed by anvil (650), for example as shown and described below in connection with FIG. 19B.

FIGS. 18 and 19A show an exemplary staple driver (690) of the staple driver member of circular stapler (600) in a fully recessed position ($D_0$) within a respective staple opening (699) of stapling head assembly (640). Though not shown, it will be appreciated that the staple driver member (not shown) of stapling head assembly (640) includes a plurality of staple drivers (690) arranged annularly similar to staple drivers (352) of staple driver member (350) described above. Each staple driver (690) is slidably arranged within a respective staple opening (699) of a deck member (698) and has an upper end that supports the crown (694) of a respective staple (692). As staple actuator (664) is driven distally by motor unit (660) in response to activation by control module (672), staple driver (690) drives the respective staple (692) distally from staple opening (699), as shown in FIGS. 19B and 19C. FIG. 19B shows staple driver (690) in a partially extended position ($D_1$) in which the upper end of staple driver (690) and the staple crown (694) are positioned at an upper end of staple opening (699), in line with deck surface (644). In this position, staple legs (696) have been received by staple forming pockets (652) of anvil (650) such that staple legs (696) are partially deformed within the tissue (not shown) clamped between anvil (650) and deck surface (644). FIG. 19C shows staple driver (690) in a fully extended position ($D_2$) in which staple legs (696) of staple (692) are fully formed against anvil (650), within the clamped tissue. As shown in FIGS. 19B and 19C, the free ends of staple legs (696) in a formed state are bent proximally toward staple crown (694).

Control module (672) of the present version is configured to initiate distal actuation of knife actuator (666) (and thus the knife member) upon determining that staple drivers (690) have reached the partially extended position ($D_2$) shown in FIG. 19B. This determination by control module (672) may be made via communication with one or more sensors configured to monitor the longitudinal position of one or more of staple actuator (664), the staple driver member, or staple drivers (690). Additionally, as noted above, calibrating the longitudinal stroke of trocar actuator (662) prior to actuating staple actuator (664) ensures that anvil (650) in the closed position defines the proper tissue gap ($\delta$) relative to deck surface (644), consistent with the target tissue gap specified via user interface (616). This in turn ensures that distal actuation of knife actuator (666) does not begin until staple legs (696) are indeed at least partially deformed by the amount expected based on the user-specified target tissue gap. This approach ensures that the clamped tissue is not disrupted via engagement by the knife member during the initial stage of staple formation. Advantageously, this enables staples (692) to form properly within the clamped tissue, thereby maximizing hemostasis along the formed staple line.

Figure 20:
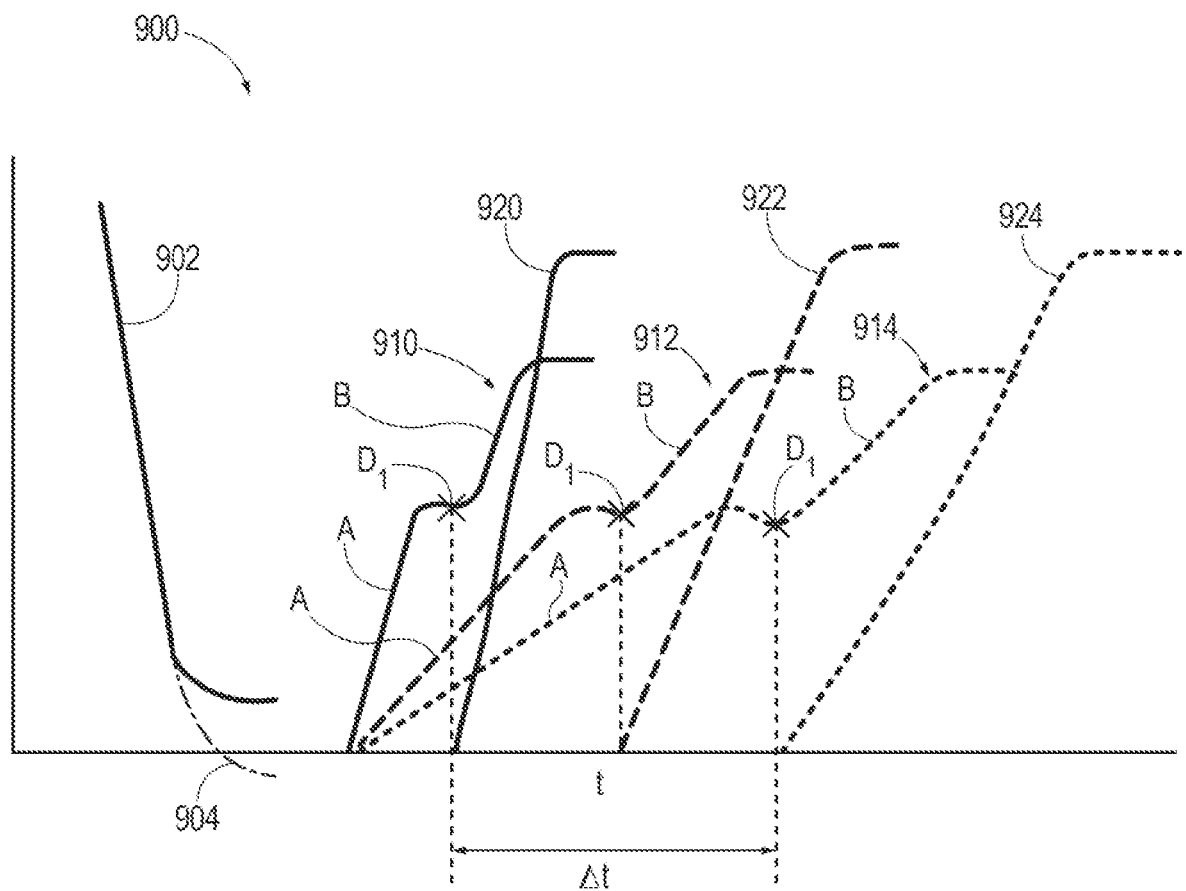
FIG. 20 depicts a line graph showing exemplary relationships between operational elements of the circular surgical stapler of FIG. 9 over time, including anvil displacement, knife displacement, and firing load on the motor unit.

FIG. 20 depicts a line graph (900) showing exemplary curves that represent actuation over time of the trocar actuator (662), staple actuator (664), and knife actuator (666) by motor unit (660) during exemplary surgical procedures on thin tissue, medium thickness tissue, and thick tissue. An anvil displacement curve (902) represents longitudinal displacement over time of trocar actuator (662), and thus trocar (642) and anvil (650). As dashed lower portion (904) of anvil displacement curve (902) represents an original intended closure stroke of anvil (650) prior to calibration of the closure member actuation algorithm in the manner described above.

A first motor load curve (910) represents electrical current load of motor unit (660) while actuating staple actuator (664) and thus the staple driver member and its staple drivers (690) to drive staples (692) distally against anvil (650), through thin tissue. A second motor load curve (912) represents electrical current load of motor unit (660) while actuating staple actuator (664) and thus the staple driver member and its staple drivers (690) to drive staples (692) distally against anvil (650), through medium thickness tissue. A third motor load curve (914) represents electrical current load of motor unit (660) while actuating staple actuator (664) and thus the staple driver member and its staple drivers (690) to drive staples (692) distally against anvil (650), through thick tissue. A first knife displacement curve (920) represents longitudinal displacement over time of knife actuator (666), and thus the knife member, through thin tissue. A second knife displacement curve (922) represents longitudinal displacement over time of knife actuator (666), and thus the knife member, through medium thickness tissue. A third knife displacement curve (924) represents longitudinal displacement over time of knife actuator (666), and thus the knife member, through thick tissue.

As shown by motor load curves (910, 912, 914) and knife displacement curves (920, 922, 924), control module (672) of the present example is configured to control motor unit (660) to actuate staple actuator (664) and knife actuator (666) distally more slowly as tissue thickness increases. This is evident in graph (900) by the horizontally elongated configuration of medium tissue thickness curves (912, 922) and thick tissue curves (914, 924) relative to thin tissue curves (910, 920). This approach ensures that the electrical current load of motor unit (660) does not exceed a predetermined threshold value during the stapling and cutting strokes. In that regard, as described above, distal actuation of staples (692) and the knife member through tissue of increasing thicknesses causes motor unit (660) to draw higher current loads.

Each motor load curve (910, 912, 914) includes a first rise (A) that reflects distal actuation of staple actuator (664) through a first portion of the stapling stroke that actuates staple drivers (690) from the full recessed position ($D_0$) to the emerging position ($D_1$), shown in FIGS. 18-19B, thus driving staples (692) through an initial stage of formation against anvil (650). Each motor load curve (910, 912, 914) further includes a second rise (B) that reflects distal actuation of staple actuator (664) through a second portion of the stapling stroke that actuates staple drivers (690) from the emerging position ($D_1$) to the fully extended position ($D_2$), shown in FIGS. 19B-19C, thus driving staples (692) distally through a final stage of formation against anvil (650). As shown by graph (900) for each of the three tissue thickness scenarios, control module (672) initiates distal actuation of knife actuator (666) to perform the cutting stroke when staple drivers (690) have reached their emerging positions ($D_1$), represented by motor load curves as the transition between first and second curve portions (A, B). As described above in connection with FIGS. 18-19C, this approach of staggering the initiation of the stapling and cutting strokes serves to mitigate risk of staple malformation, thus ensuring properly formed staples in patient tissue. In the present example, graph (900) shows an exemplary time difference (Δt) between initiation of knife actuator (666) in a procedure on thin tissue and initiation of knife actuator (666) in a procedure on thick tissue.

In versions of circular stapler (600) in which sensor (674) includes a current sensor operatively coupled with motor unit (660) in the manner described above, control module (672) may control an actuation rate (or "velocity") of one or more actuators (662, 664, 666) and their corresponding components based on the electrical current drawn by motor unit (660) as detected by the current sensor. For instance, in response to an increase in detected current load above a predetermined threshold, control module (672) may decrease the actuation rate of the actuator (662, 664, 666) being actuated. Similarly, in versions of stapler (600) where sensor (674) includes a force sensor operatively coupled with one or more of trocar actuator (662), staple actuator (664), knife actuator (666), or their related components (e.g., trocar (642)), control module (672) may be configured to decrease an actuation rate of a particular actuator (662, 664, 666) in response to detecting an increase in longitudinal force exerted on that actuator (662, 664, 666) during actuation thereof.

It will be appreciated that the actuation rates of one or more actuators (662, 664, 666) may be controlled based on additional factors as well, such as a size of stapling head assembly (640) or a target tissue gap specified by a user via user interface (616). By way of example only, control module (672) may decrease the actuation rates of one or more actuators (662, 664, 666) in the presence of a stapling head assembly (640) of a relatively larger diameter; and increase the actuation rates of one or more actuators (662, 664, 666) in the presence of a stapling head assembly (640) of a relatively smaller diameter. Additionally, control module (672) may decrease the actuation rates of one or more actuators (662, 664, 666) for larger tissue gaps and increase the actuation rates of one or more actuators (662, 664, 666) for smaller tissue gaps.

V. Exemplary Identification of Stapling Head Assembly Via Radio Frequency Identification As described above, it may be desirable in some instances to detect certain characteristics of stapling head assembly (640) (e.g., diameter) via sensor (674) and communicate such information to control module (672), particularly in instances in which stapling head assemblies (640) of various different types are interchangeable with shaft assembly (630). As shown in FIG. 9, end effector (640, 650) of surgical instrument (600) may include a radio frequency identification (RFID) tag (1000) configured to store information pertaining to selected characteristics of end effector (640, 650). Additionally, one of shaft assembly (630) or handle assembly (610) may include a sensor (674) in the form of an RFID scanner configured to read the information stored by RFID tag (1000) and communicate such information to control module (672). Based on such information, control module (672) may suitably adjust one or more actuation algorithms of actuators (662, 664, 666) to ensure appropriate longitudinal displacements, actuation rates, and/or time pauses between strokes of actuators (662, 664, 666), for example as described in greater detail below and in U.S. Provisional Pat. App. No. U.S. Provisional Pat. App. No. 62/868,457, incorporated by reference above.

As shown in FIG. 21, a graph (2260) represents a relationship between firing Load (lbs) on the Y-axis and firing time (sec) on the X-axis. Graph 21 depicts a default, unadjusted, firing algorithm (2263) and an adjusted firing algorithm (2263). The graph 2260 further depicts a default maximum firing load threshold (2261) (e.g. 400 lbs) and a final maximum firing load threshold (2262) (e.g. 485 lbs) for a firing load applied by motor unit (660) to stapling head assembly (640), via staple actuator (664) and knife actuator (666). The default maximum firing load threshold (2261) is adjusted to the final maximum firing load threshold (2262) based on end-effector information of the end effector (640, 650) that is stored in RFID tag (1000) of stapling head assembly (640) and read by RFID scanner (674). In the example of FIG. 21, the end-effector information represents a stapling head assembly (640) (or "staple cartridge") that comprises a larger size (e.g. 31 mm) than a default staple cartridge (e.g. 25 mm). The default staple cartridge size (e.g. 25 mm) is associated with the default firing algorithm (2263) and default maximum firing load threshold (2261). Meanwhile, the larger staple cartridge size (e.g. 31 mm) is associated with the final firing algorithm (2264) and final maximum firing load threshold (2262).

The end-effector information stored in the RFID tag (1000) can include the staple cartridge size and/or a firing load adjustment value (e.g. 85 lbs) based on the cartridge size. In the event of the staple cartridge size, the control module (672) can use a database or a lookup table of staple cartridge sizes and corresponding firing load adjustment values to look up a suitable firing load adjustment values.

Further, input from the RFID scanner (674) indicative of the end-effector information causes the control module (672) to adjust the default maximum firing load threshold (2261) (e.g. 400) to the final maximum firing load threshold (2262) (e.g. 485 lbs), and maintain a firing algorithm (2264) below the final maximum firing load threshold (2262), as illustrated in FIG. 21.

In the example of FIG. 21, the control module (672) adjusts or introduces a minimum wait-time "t" before causing the motor unit (660) to apply the firing algorithm (2263) to the end effector (640, 650). In various instances, the minimum wait-time "t" is a time period between completion of a closure sequence of an end effector of the surgical instrument (600), where tissue is grasped by the end effector (640, 650) in a closed configuration, and commencement of a firing sequence of the end effector (640, 650), where the grasped tissue is stapled and cut. The minimum wait time "t" permits tissue creep where the grasped tissue adjusts to a lower average pressure thereby reducing the maximum firing load necessary to complete the firing sequence of the end effector (640, 650) to a value at or below the final maximum firing load threshold (2262). In the default firing algorithm (2263), without the minimum wait-time "t", the firing algorithm (2263) must be interrupted (2267) for a time period from time t3 to time t4 to prevent the firing load from exceeding the final maximum firing load threshold (2262).

By comparison, the firing algorithm (2264) is continued through the time period between t3 and t4, as illustrated in FIG. 21.

Referring still to FIG. 21, another factor that can influence the minimum wait time "t" is the user-selected form height of the staples (692) deployed from the stapling head assembly (640), which is directly proportional to tissue gap distance defined by anvil (650) in the closed position, as described above. As also described above, control module (672) may be configured to prompt a user through user interface (616) to select a desired staple form height (i.e., tissue gap). In at least one example, the control module (672) can present the user with a plurality of staple form heights from which to select. Additionally, or alternatively, the control module (672) can recommend an optimal form height based on the tissue being treated by the surgical instrument (600). In any event, the user-selected form height can cause the control module (672) to further adjust the minimum wait time "t". In at least one example, the control module (672) stores, in a database or a lookup table, form heights and corresponding wait-time adjustments. The control module (672) can adjust the minimum wait time "t" by identifying a wait-time adjustment associated with a user-selected form height, and then adjusting the minimum wait time "t" in accordance with the identified wait-time adjustment.

Generally, a more formed staple is associated with a greater firing load, and requires a greater minimum wait time "t" than a lesser formed staple. In the example of FIG. 21, the user-selected form height (2265) is associated with a firing load "F2", and is greater than a minimum form height (2266) associated with a minimum firing load "F1". The minimum firing loads "F 1" and "F2" represent firing loads at which staple legs begin to buckle. Accordingly, in the example illustrated in FIG. 21, the selected wait time "t" is a result of the selected larger size staple cartridge and the selected form height (2265).

VI. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of operating a powered surgical stapler having a motor unit, a controller in communication with the motor unit, and a stapling assembly operatively coupled with the motor unit and having a closure member, a staple driver member, and a knife member, wherein the stapling assembly is actuatable between an open state for receiving tissue and a closed state for clamping tissue, the method comprising: (a) receiving with the controller a user input that indicates a tissue gap to be defined by the stapling assembly in the closed state; (b) based on the user input, controlling the motor unit to actuate the closure member to transition the stapling assembly to the closed state to define the tissue gap and clamp tissue therein; (c) with the stapling assembly in the closed state, controlling the motor unit to actuate the staple driver member to drive staples into the clamped tissue; (d) after initiating actuation of the staple driver member, determining with the controller that the staple driver member has reached a predetermined longitudinal position; and (e) in response to the determination, controlling the motor unit to initiate actuation of the knife member to cut the clamped tissue.

Example 2

The method of Example 1, wherein the closure member, the staple driver member, and the knife member are actuatable by the motor unit independently of one another.

Example 3

The method of any of the preceding Examples, wherein actuating the staple driver member to drive staples into the clamped tissue and actuating the knife member to cut the clamped tissue comprise actuating the staple driver member and the knife member distally relative to the motor unit.

Example 4

The method of any of the preceding Examples, wherein the stapling assembly includes an anvil, wherein each staple includes a crown and a pair of legs, wherein the predetermined longitudinal position of the staple driver member comprises a position in which the legs have been at least partially deformed by the anvil.

Example 5

The method of Example 4, wherein the stapling assembly includes a deck surface having a plurality of openings that house the staples, wherein the predetermined longitudinal position of the staple driver member comprises a position in which the crowns of the staples are positioned at the deck surface.

Example 6

The method of any of the preceding Examples, wherein the staple driver member is actuatable distally through a stapling stroke, wherein the knife member is actuatable distally through a cutting stroke, wherein controlling the motor unit to initiate actuation of the knife member comprises initiating the cutting stroke before completion of the stapling stroke.

Example 7

The method of any of the preceding Examples, wherein the stapling assembly includes a sensor in communication with the controller, wherein the method further comprises controlling actuation of at least one of the closure member, the staple driver member, or the knife member in response to a signal provided to the controller by the sensor.

Example 8

The method of Example 7, wherein the method further comprises detecting with the sensor that the staple driver member has reached the predetermined longitudinal position.

Example 9

The method of any of the preceding Examples, wherein the method further comprises detecting with the sensor that the tissue gap indicated by the user input has been achieved by the stapling assembly.

Example 10

The method of any of the preceding Examples, wherein the stapling assembly includes a current sensor operatively coupled with the motor unit and the controller, wherein the method further comprises controlling a rate of actuation of at least one of the closure member, the staple driver member, or the knife member based on a signal provided by the current sensor, wherein the signal indicates an electrical current drawn by the motor unit.

Example 11

The method of Example 10, wherein controlling the rate of actuation based on the signal provided by the current sensor includes decreasing the rate of actuation in response to detection by the current sensor of an increase in electrical current drawn by the motor unit.

Example 12

The method of any of the preceding Examples, further comprising controlling a longitudinal displacement of at least one of the closure member, the staple driver member, or the knife member based on the user input.

Example 13

The method of any of the preceding Examples, further comprising controlling a rate of actuation of at least one of the closure member, the staple driver member, or the knife member based on the user input.

Example 14

The method of any of the preceding Examples, wherein the controller is configured to store and execute a closure member actuation algorithm to actuate the closure member via the motor unit to transition the stapling assembly to the closed state, wherein the method further comprises: (a) while actuating the closure member from a first longitudinal position to a second longitudinal position, comparing with the controller an actual longitudinal displacement of the closure member to an expected longitudinal displacement stored by the controller; (b) determining with the controller that the actual longitudinal displacement differs from the expected longitudinal displacement by a difference value; and (c) adjusting the closure member actuation algorithm with the controller based on the difference value.

Example 15

The method of any of the preceding Examples, wherein the controller is configured to store and execute a staple driver member actuation algorithm to actuate the staple driver member longitudinally to drive the staples into the clamped tissue, and a knife member actuation algorithm to actuate the knife member longitudinally to cut the clamped tissue, wherein the method further comprises adjusting with the controller at least one of the staple driver member actuation algorithm or the knife member actuation algorithm based on the difference value.

Example 16

A method of operating a powered surgical stapler having a motor unit, a controller in communication with the motor unit, and a stapling assembly operatively coupled with the motor unit, wherein the stapling assembly includes a closure member, a staple driver member, a knife member, a deck surface having a plurality of staple openings, and a plurality of staples housed within the staple openings, wherein the stapling assembly is actuatable between an open state for receiving tissue and a closed state for clamping tissue, the method comprising: (a) receiving with the controller a user input that indicates a tissue gap to be defined by the stapling assembly in the closed state; (b) based on the user input, controlling the motor unit to actuate the closure member to transition the stapling assembly to the closed state to define the tissue gap and clamp tissue therein; (c) with the stapling assembly in the closed state, controlling the motor unit to actuate the staple driver member to drive the staples from the staple openings into the clamped tissue; and (d) in response to the staples reaching a predetermined longitudinal position relative to the deck surface, controlling the motor unit to initiate actuation of the knife member to cut the clamped tissue.

Example 17

The method of Example 16, wherein the stapling assembly includes a sensor in communication with the controller, wherein the method further comprises detecting with the sensor that the staples have reached the predetermined longitudinal position.

Example 18

The method of any of Examples 16 through 17, further comprising controlling at least one of a rate of actuation of the knife member or a longitudinal displacement of the knife member based on the user input.

Example 19

A method of operating a powered surgical stapler having a motor unit, a controller in communication with the motor unit, and a stapling assembly operatively coupled with the motor unit and having a closure member, a staple driver member, and a knife member, wherein the stapling assembly is actuatable between an open state for receiving tissue and a closed state for clamping tissue, the method comprising: (a) receiving with the controller a user input that indicates a tissue gap to be defined by the stapling assembly in the closed state; (b) based on the user input, controlling the motor unit to actuate the closure member to transition the stapling assembly to the closed state to define the tissue gap and clamp tissue therein; (c) with the stapling assembly in the closed state, controlling the motor unit to actuate the staple driver member to drive staples into the clamped tissue; and (d) after initiating actuation of the staple driver member, controlling the motor unit based on the user input to actuate the knife member to cut the clamped tissue.

Example 20

The method of Example 19, wherein controlling the motor unit based on the user input to actuate the knife member comprises controlling at least one of a longitudinal displacement or a rate of actuation of the knife member based on the user input.

VII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 16/574,773, entitled "Method for Calibrating Movements of Actuated Members of Powered Surgical Stapler," filed on Sep. 18, 2019, published as U.S. Pub. No. 2021/0077111 on Mar. 18, 2021, issued as U.S. Pat. No. 11,645,516 on Oct. 11, 2002; U.S. patent application Ser. No. 16/574,281, entitled "Method for Controlling End Effector Closure for Powered Surgical Stapler," filed on Sep. 18, 2019, published as U.S. Pub. No. 2021/0077110 on Mar. 18, 2021, issued as U.S. Pat. No. 11,185,331 on Nov. 30, 2021; and U.S. patent application Ser. No. 16/574,299, entitled "Anvil Retention and Release Features for Powered Circular Surgical Stapler," filed on Sep. 18, 2019, published as U.S. Pub. No. 2021/0077093 on Mar. 18, 2021, issued as U.S. Pat. No. 11,185,324 on Nov. 30, 2021. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
 (a) a controller;
 (b) a motor unit in communication with the controller, wherein the motor unit includes at least one motor; and
 (c) an end effector operatively coupled with the motor unit and configured to clamp, staple, and cut tissue, wherein the end effector comprises:
  (i) a closure member actuatable by the motor unit to transition the end effector from an open state to a closed state to clamp tissue,
  (ii) a staple driver member actuatable by the motor unit to drive a plurality of staples into the clamped tissue, and
  (iii) a knife member actuatable by the motor unit to cut the clamped tissue,
 wherein the controller is configured to:
  (i) control the motor unit to actuate the end effector from the open state to the closed state to clamp tissue,
  (ii) in response to determining that the end effector has assumed the closed state, control the motor unit to actuate the staple driver member from a first position to a second position to staple the clamped tissue, and
  (iii) in response to determining that the staple driver member has advanced at least partially toward the second position, control the motor unit to initiate actuation of the knife member to cut the clamped tissue.

2. The apparatus of claim 1, wherein the end effector further comprises:
   (i) a first stapling surface having a plurality of staple openings that house a plurality of staples, and
   (ii) a second stapling surface having a plurality of staple forming pockets configured to form the staples,
   wherein at least one of the first or second stapling surfaces is actuatable by the motor unit to transition the end effector from the open state to the closed state.

3. The apparatus of claim 2, wherein the controller is configured to receive a user input, wherein the motor unit is controllable by the controller to achieve a closed state defining a predetermined tissue gap between the first and second stapling surfaces, wherein the predetermined tissue gap is based on the user input.

4. The apparatus of claim 1, wherein the closure member, the staple driver member, and the knife member are actuatable by the motor unit independently of one another.

5. The apparatus of claim 4, wherein the staple driver member is actuatable through a stapling stroke and the knife member is actuatable through a cutting stroke, wherein the controller is configured to initiate the cutting stroke before completion of the stapling stroke.

6. The apparatus of claim 1, wherein the controller is configured to, in response to determining that the staple driver member has advanced to a predetermined longitudinal position, initiate actuation of the knife member.

7. The apparatus of claim 6, wherein the end effector includes an anvil, wherein each staple includes a crown and a pair of legs, wherein the predetermined longitudinal position of the staple driver member comprises a position in which the legs of the staples have been at least partially formed by the anvil.

8. The apparatus of claim 6, wherein the stapling assembly includes a deck surface having a plurality of openings that house the staples, wherein the predetermined longitudinal position of the staple driver member comprises a position at which the crowns of the staples are positioned at the deck surface.

9. The apparatus of claim 1, further comprising a position sensor operatively coupled with the controller, wherein the position sensor is configured to detect a longitudinal position of at least one of the closure member or the staple driver member, wherein the controller is configured to control the motor unit based on the detected longitudinal position.

10. The apparatus of claim 9, wherein the sensor is configured to detect a longitudinal position of the closure member, wherein the controller is configured to control the motor unit to actuate the closure member to transition the end effector to a closed state in which the end effector defines a predetermined tissue gap.

11. The apparatus of claim 10, wherein the controller is configured to receive a user input, wherein the predetermined tissue gap is based on the user input.

12. The apparatus of claim 1, further comprising a current sensor operatively coupled with the motor unit and the controller and configured to measure an electrical current drawn by the motor unit, wherein the controller is configured to control a rate of actuation of at least one of the closure member, the staple driver member, or the knife member based on an electrical current measured by the current sensor.

13. The apparatus of claim 12, wherein the controller is configured to decrease the rate of actuation in response to the current sensor detecting an increase in electrical current drawn by the motor unit.

14. The apparatus of claim 1, wherein the controller is configured to receive a user input, wherein the controller is configured to control at least one of the following based on the user input:
   (i) a longitudinal displacement of at least one of the closure member, the staple driver member, or the knife member, or
   (ii) a rate of actuation of at least one of the closure member, the staple driver member, or the knife member.

15. The apparatus of claim 1, wherein the controller is configured to store and execute a closure member actuation algorithm to actuate the closure member via the motor unit to transition the end effector from the open state to the closed state, wherein the controller is further configured to:
   (i) while the closure member advances from a first longitudinal position to a second longitudinal position, compare an actual longitudinal displacement of the closure member to an expected longitudinal displacement,
   (ii) determine whether the actual longitudinal displacement differs from the expected longitudinal displacement by a difference value, and
   (iii) adjust the closure member actuation algorithm based on the difference value.

16. The apparatus of claim 15, wherein the controller is further configured to:
   (i) store and execute a staple driver member actuation algorithm to actuate the staple driver member to drive the staples into the clamped tissue,
   (ii) store and execute a knife member actuation algorithm to actuate the knife member to cut the clamped tissue, and
   (iii) adjust at least one of the staple driver member actuation algorithm or the knife member actuation algorithm based on the difference value.

17. An apparatus comprising:
   (a) a controller configured to receive a user input;
   (b) a motor unit in communication with the controller, wherein the motor unit includes at least one motor; and
   (c) an end effector operatively coupled with the motor unit, wherein the end effector comprises:
      (i) a first stapling surface having a plurality of staple openings that house a plurality of staples,
      (ii) a second stapling surface having a plurality of staple forming pockets configured to form the staples,
      (iii) a closure member actuatable by the motor unit to drive the first and second stapling surfaces relative to one another from an open state to a closed state to clamp tissue positioned between the first and second stapling surfaces,
      (iv) a staple driver member actuatable by the motor unit to drive staples into the clamped tissue, and
      (v) a knife member actuatable by the motor unit to cut the clamped tissue,
   wherein the controller is configured to:
      (i) control the motor unit to actuate the end effector from the open state to the closed state in which the first and second stapling surfaces define a predetermined tissue gap based on the user input,
      (ii) in response to determining that the end effector has assumed the closed state, control the motor unit to actuate the staple driver member from a first position to a second position to staple the clamped tissue, and (iii) in response to determining that the staple driver member has advanced to a predetermined longitudinal position, control the motor unit to initiate actuation of the knife member to cut the clamped tissue.

18. The apparatus of claim 17, wherein the staple driver member is actuatable through a stapling stroke, wherein the controller is configured to initiate actuation of the knife member after initiation of the stapling stroke and before completion of the stapling stroke.

19. An apparatus comprising:
(a) a controller configured to receive a user input;
(b) a motor unit in communication with the controller, wherein the motor unit includes at least one motor; and
(c) an end effector operatively coupled with the motor unit and configured to clamp, staple, and cut tissue, wherein the end effector comprises:
  (i) a closure member actuatable by the motor unit to transition the end effector from an open state to a closed state to clamp tissue,
  (ii) a staple driver member actuatable by the motor unit to drive a plurality of staples into the clamped tissue, and
  (iii) a knife member actuatable by the motor unit to cut the clamped tissue,
wherein the controller is configured to:
  (i) control the motor unit to actuate the end effector from the open state to the closed state to clamp tissue,
  (ii) control the motor unit to actuate the staple driver member to staple the clamped tissue, and
  (iii) control the motor unit to actuate the knife member to cut the clamped tissue, wherein the controller is configured to control at least one of the following based on the user input:
    (A) a timing of the actuation initiation of the knife member,
    (B) a longitudinal displacement of the knife member, or
    (C) a rate of actuation of the knife member.

20. The apparatus of claim 19, wherein the controller is further configured to control a tissue gap distance of the end effector in the close state based on the user input.

* * * * *